United States Patent
Xi et al.

(10) Patent No.: US 12,257,265 B2
(45) Date of Patent: Mar. 25, 2025

(54) CYCLIC DINUCLEOTIDE PRODRUG MOLECULE, PREPARATION METHOD THEREFOR AND APPLICATION THEREOF

(71) Applicant: SHENZHEN YING BIOPHARMACEUTICAL CO., LTD., Shenzen (CN)

(72) Inventors: Zhen Xi, Tianjin (CN); Zhenghua Wang, Tianjin (CN); Dan Wang, Tianjin (CN)

(73) Assignee: SHENZHEN YING BIOPHARMACEUTICAL CO., LTD, Shenzhen (CN)

( * ) Notice: Subject to any disclaimer, the term of this patent is extended or adjusted under 35 U.S.C. 154(b) by 800 days.

(21) Appl. No.: 17/422,137

(22) PCT Filed: Jan. 10, 2020

(86) PCT No.: PCT/CN2020/071329
§ 371 (c)(1),
(2) Date: Jul. 9, 2021

(87) PCT Pub. No.: WO2020/143740
PCT Pub. Date: Jul. 16, 2020

(65) Prior Publication Data
US 2022/0125821 A1    Apr. 28, 2022

(30) Foreign Application Priority Data

Jan. 10, 2019 (CN) .......................... 201910023472.1

(51) Int. Cl.
*C08B 37/00* (2006.01)
*A61K 31/7088* (2006.01)
(Continued)

(52) U.S. Cl.
CPC .......... *A61K 31/7088* (2013.01); *A61P 35/00* (2018.01); *C07H 1/00* (2013.01); *C07H 19/213* (2013.01); *C07H 21/04* (2013.01)

(58) Field of Classification Search
CPC .. A61K 31/7088; A61K 31/7084; C07H 1/00; C07H 19/213; C07H 19/07;
(Continued)

(56) References Cited

U.S. PATENT DOCUMENTS 9,905,856 B1    2/2018 Zhamu et al.
2018/0354983 A1*  12/2018 Vernejoul .............. C07H 21/02
2019/0027788 A1    1/2019 Liu et al.

FOREIGN PATENT DOCUMENTS

CN    102596204 A    7/2012
CN    107849084 A    3/2018
(Continued)

OTHER PUBLICATIONS

Holley et al, Journal of The American Chemical Society, 1952, Jun. 20, vol. 74, 3069-3074.*

(Continued)

*Primary Examiner* — Ganapathy Krishnan
(74) *Attorney, Agent, or Firm* — Calfee, Halter & Griswold LLP

(57) ABSTRACT

Disclosed are a cyclic dinucleotide prodrug molecule, a preparation method therefor and an application thereof relating to the field of pharmaceuticals. The cyclic dinucleotide prodrug molecule has a structure shown in formula I, II, or III, can freely cross cell membranes and release cyclic dinucleotide, and has high cell activity.

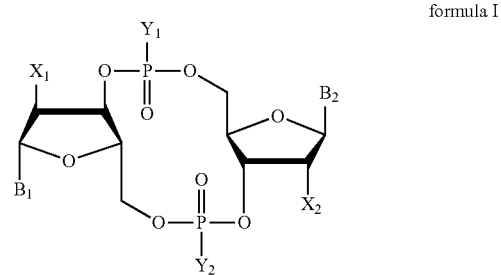

formula I

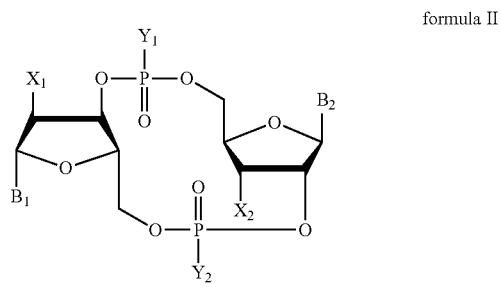

formula II

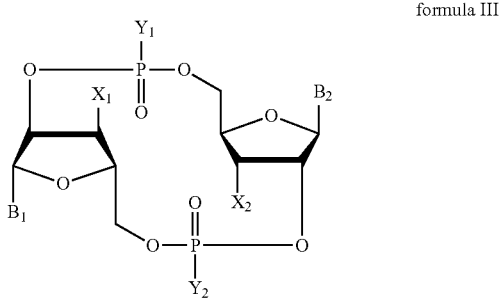

formula III

11 Claims, 5 Drawing Sheets

(51) Int. Cl.
*A61P 35/00* (2006.01)
*C07H 1/00* (2006.01)
*C07H 19/213* (2006.01)
*C07H 21/04* (2006.01)

(58) Field of Classification Search
CPC ...... C07H 19/207; C07H 21/00; C07H 21/04; A61P 35/00; A61P 31/04; A61P 31/12

USPC .................................................. 514/45, 44 R
See application file for complete search history.

(56) References Cited

FOREIGN PATENT DOCUMENTS

| WO | 2011005761 A1 | 1/2011 | |
|---|---|---|---|
| WO | WO 2014/189805 A1 * | 11/2014 | ......... A61K 31/7084 |
| WO | 2016096174 A8 | 6/2016 | |
| WO | 2017027645 A1 | 2/2017 | |
| WO | WO 2017/093933 A1 * | 6/2017 | ......... A61K 31/7084 |
| WO | 2018009648 A1 | 1/2018 | |

OTHER PUBLICATIONS

International Search Report of PCT/CN2020/071329 dated Mar. 31, 2020 (3 pages).
Wang, Baifan, et al. "Computational and NMR Spectroscopy Insights into the Conformation of Cyclic di-Nucleotides", Scientific Reports. vol. 7, No. 1, Nov. 29, 2017.
Wang et al., "Computational and NMR spectroscopy insights into the conformation of cyclic di-nucleotides," Scientific Reports, 7, 16550 (2017), 11 pages.
Polidarova et al., "Synthesis and Biological Evaluation of Phosphoester and Phosphorothioate Prodrugs of STING Agonist 3',3'-c-Di(2'F,2'dAMP)," Journal of Medicinal Chemistry, 64 (2021), pp. 7596-7616.
Xie et al., "S-acylthioalkyl ester (SATE)-based prodrugs of deoxyribose cyclic dinucleotides (dCDNs) as the STING agonist for antitumor immunotherapy," European Journal of Medicinal Chemistry, 243 (2022), 15 pages.
Xie et al., "Dithioethanol (DTE)-Conjugated Deoxyribose Cyclic Dinucleotide Prodrugs (DTE-dCDNs) as STING Agonist," International Journal of Molecular Sciences, 25, 86 (2024), 15 pages and Supporting Information pp. S1-S22.
Meade et al., "Efficient delivery of rNAi prodrugs containing reversible charge-neutralizing phosphotriester backbone modifications," Nature Biotechnology, Advance Online Publication (2014), 8 pages.

* cited by examiner

CYCLIC DINUCLEOTIDE PRODRUG MOLECULE, PREPARATION METHOD THEREFOR AND APPLICATION THEREOF

CROSS-REFERENCE TO RELATED APPLICATIONS

This application is a 371 of PCT Application No. PCT/CN2020/071329 filed on Jan. 10, 2020, which claims priority to Chinese Application No. 201910023472.1, filed Jan. 10, 2019, the contents of which are hereby incorporated by reference as if recited in their entirety.

TECHNICAL FIELD

The invention relates to the field of medicines, in particular to a cyclic dinucleotide prodrug molecule, a preparation method of the cyclic dinucleotide prodrug molecule and application of the cyclic dinucleotide prodrug molecule.

BACKGROUND

Cyclic dinucleotides, a novel class of second messenger molecules found in bacteria and mammals. In mammalian cells, cyclic dinucleotides can bind to stimulator of interferon genes (STING) and stimulate an immune response. It can cause the expression of cell cytokines such as interferon-β and NF-κB, and promote the proliferation, differentiation and maturation of $CD8^+$ T cells.

Because cyclic dinucleotides have a powerful immune stimulatory effect, they can be used in the treatment of viral and bacterial infections as well as cancer. Especially, the combination with the traditional immunotherapy can show better anticancer effect. Aduro Inc. and Novartis' ADU-S100 currently enters clinical phase II and MK-1454 from MSD has already entered clinical phase I.

The cyclic dinucleotide has two phosphodiester bonds in the molecular structure. The phosphodiester bond with negative charge causes poor lipid solubility of the drug, which prevents the cyclic dinucleotide from effectively crossing cell membranes. And the phosphodiester bond is easy to be hydrolyzed, thereby causing instability of the drug molecule in the circulatory system.

Currently, auxiliary materials are mainly adopted for cyclic dinucleotide drug delivery systems. For example, early literature reported that a cyclic dinucleotide synthetase using lentivirus or adenovirus is used to promote an immune response by enzymatically synthesizing the cyclic dinucleotide after entering a cell. But this method has a large risk and is not widely used.

Delivery of cyclic dinucleotide drugs by using liposomes or lipid nanoparticles, cell penetrating peptides, protein gels containing polycationic amino acids, etc. as carriers have been reported. But the use of such carriers may reduce drug loading efficiency, and the introduction of carriers may cause some potential cytotoxicity.

The current method for solving the problem of effective uptake of cyclic dinucleotide by cells clinically is intratumoral injection. Although the direct intratumoral injection is reported in the article that the cyclic dinucleotide can be uptaken by the cells, the uptake efficiency is low, so that a larger dose of administration is needed. The administration of the large dose can cause over-activation of the immune system, thereby causing systemic or local inflammatory response.

Therefore, there are still some problems how to solve the efficient uptake of cyclic dinucleotides by cells.

SUMMARY OF THE INVENTION

The invention aims to overcome the defect that cyclic dinucleotides are difficult to be effectively taken up by cells in the prior art.

In order to achieve the above objects, the present invention provides a cyclic dinucleotide prodrug molecule, or a stereoisomer, a tautomer, a nitrogen oxide, a solvate, a metabolite, a pharmaceutically acceptable salt thereof, having a structure as shown in formula I, formula II, or formula III:

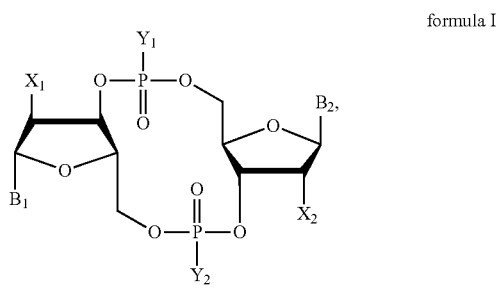

formula I

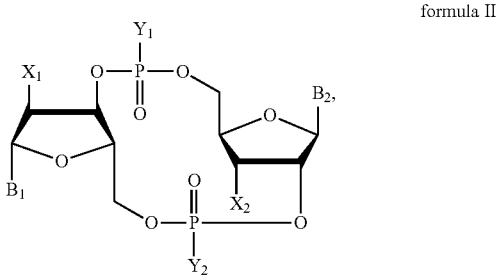

formula II

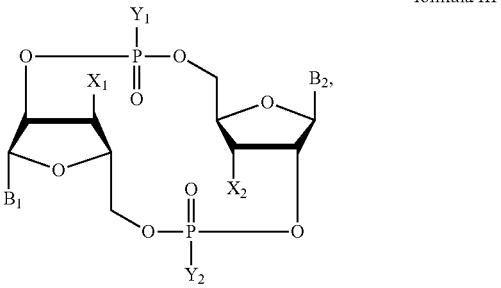

formula III in the formula I to formula III,
each of $B_1$ and $B_2$ is independently a natural base or an artificially modified base; the natural base is selected from the group consisting of guanine, adenine, cytosine, thymine, and uracil; the artificially modified base is obtained by modifying a functional group by a thio, halogenation or methylation method, wherein the functional group is a nitroindole group, an aminoindole group, a xanthine group or a hypoxanthine group;
each of $X_1$ and $X_2$ is independently —H, —$OCH_3$, or —F;
each $Y_1$ and $Y_2$ is independently selected from

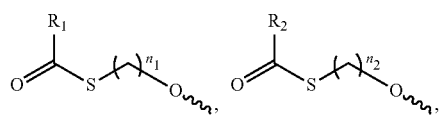

-continued

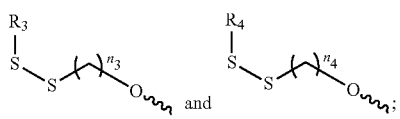

wherein, $R_1$, $R_2$, $R_3$ and $R_4$ are each independently selected from substituted or unsubstituted aliphatic hydrocarbon radicals of $C_1$-$C_{10}$, substituted or unsubstituted aromatic hydrocarbon radicals of $C_6$-$C_{11}$, five-membered or six-membered heterocyclic radicals; and the substituents optionally present in $R_1$, $R_2$, $R_3$ and $R_4$ are each independently selected from the group consisting of $C_1$-$C_5$ alkyl, $C_1$-$C_5$ alkoxy and halogen;

$n_1$, $n_2$, $n_3$ and $n_4$ are each independently integers of 1 to 5.

In a second aspect, the invention provides a method of preparing a cyclic dinucleotide prodrug molecule as hereinbefore described, the method including:

a) carrying out a first contact reaction on a first nucleotide monomer compound, a second nucleotide monomer compound and a first condensing agent in a first liquid reaction medium to obtain a linear dinucleotide intermediate;

b) under the alkaline condition, the linear dinucleotide intermediate is subjected to decyanoethyl reaction, and then the obtained reaction product and a second condensing agent are subjected to second contact reaction in a second liquid reaction medium;

c) carrying out deprotection reaction on the cyclic dinucleotide prodrug molecule with the protecting group obtained after the second contact reaction is carried out;

wherein the first nucleotide monomer compound has a structure represented by formula (13) or formula (14):

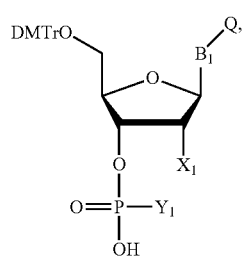

formula (13)

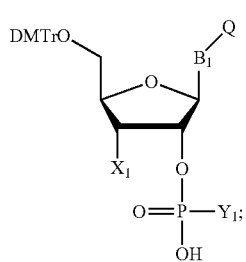

formula (14)

the second nucleotide monomer compound has a structure represented by formula (15) or formula (16):

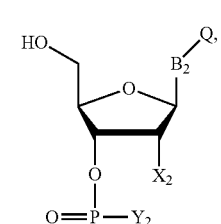

formula (15)

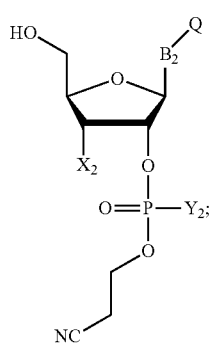

formula (16)

wherein Q represents a protecting group on an exocyclic amino group in bases represented by $B_1$ and $B_2$, and each of Q in the formula (13) to formula (16) is independently an acyl group.

In a third aspect, the present invention provides a cyclic dinucleotide prodrug molecule as described above, or a stereoisomer, a tautomer, a nitrogen oxide, a solvate, a metabolite, a pharmaceutically acceptable salt thereof, for the preparation of a drug.

The cyclic dinucleotide prodrug molecule provided by the invention can automatically cross cell membranes and release the cyclic dinucleotide, and it has higher cell activity.

DRAWINGS

Figure 4:
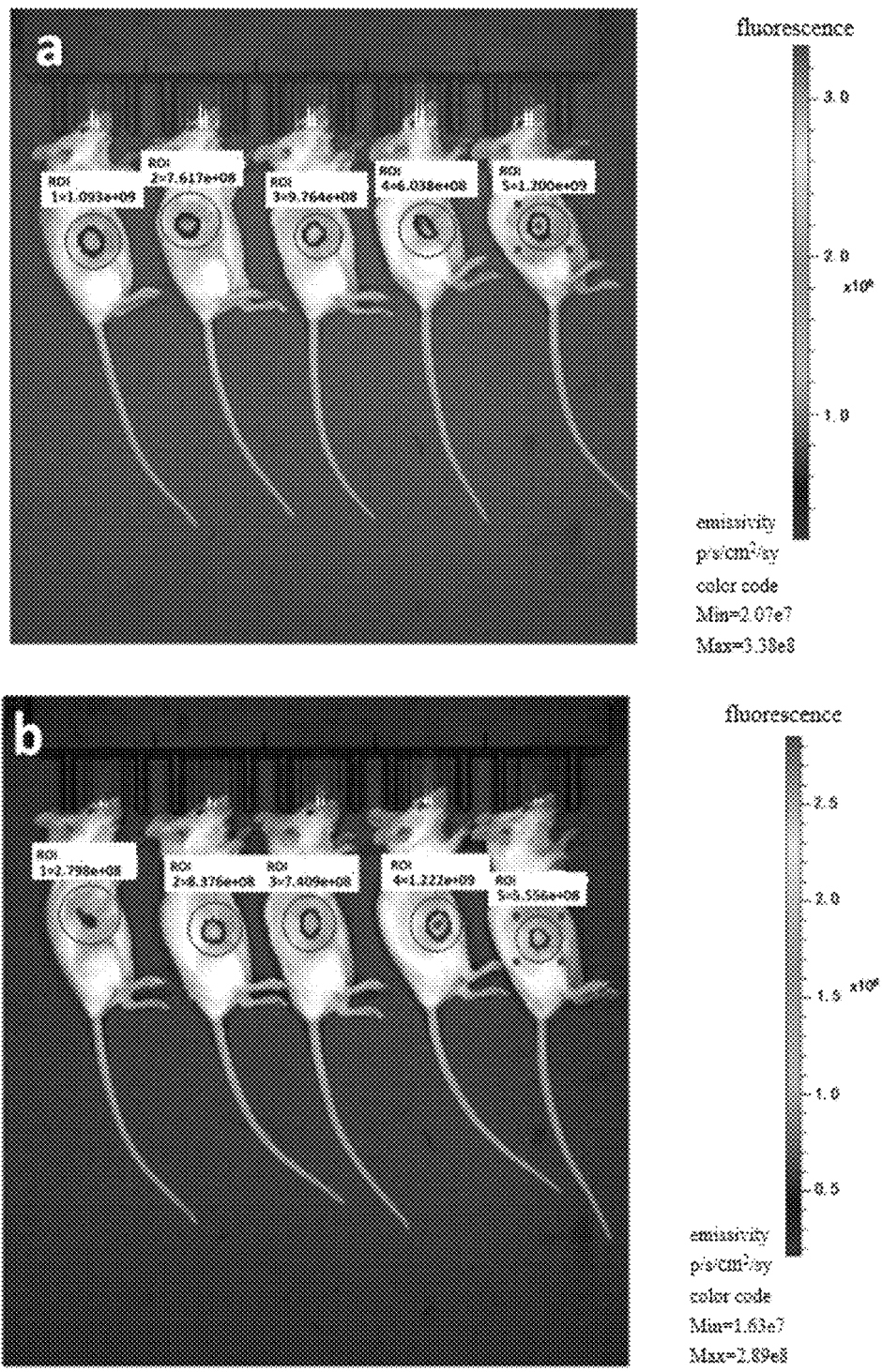
Figure 4:
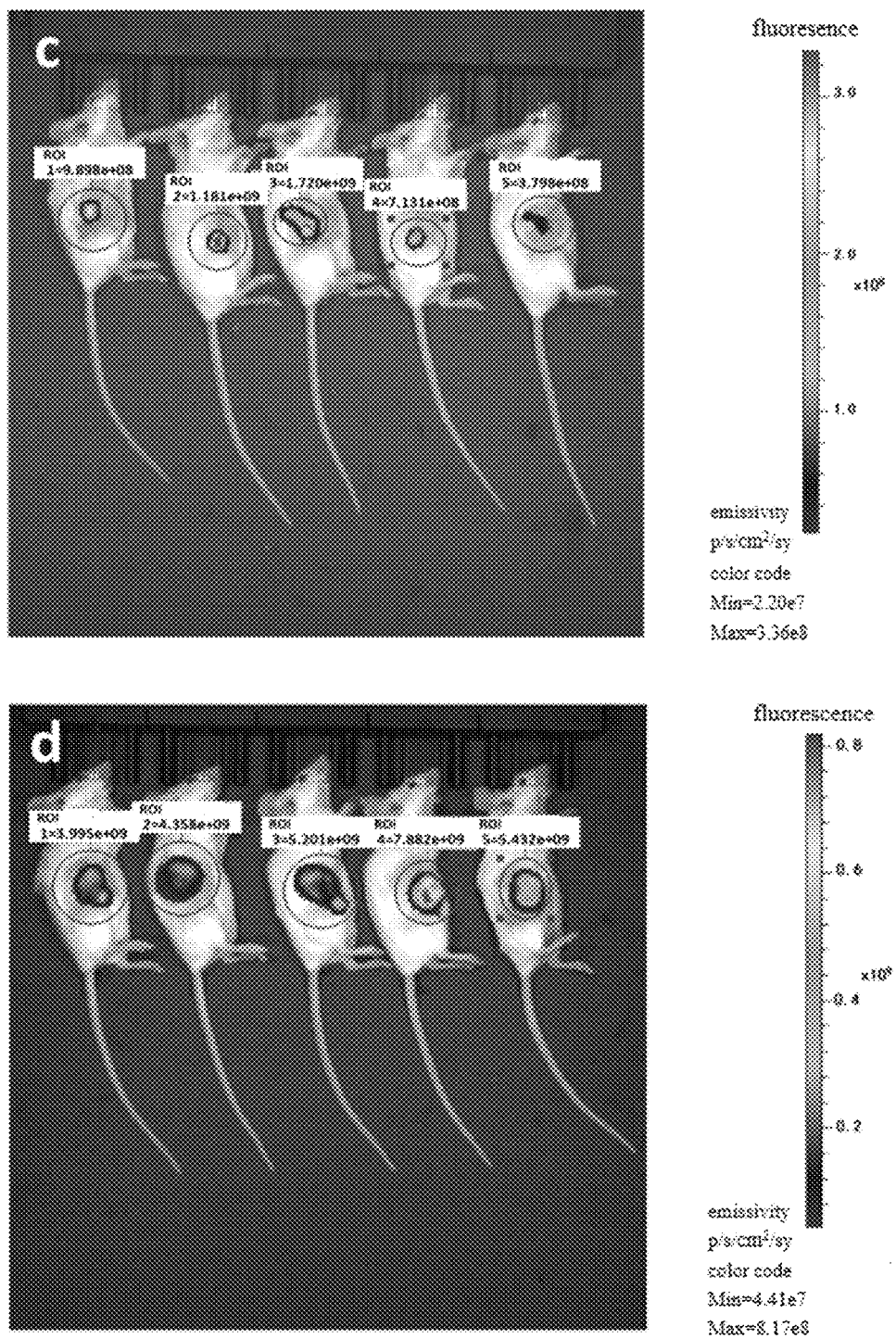
Figure 4:
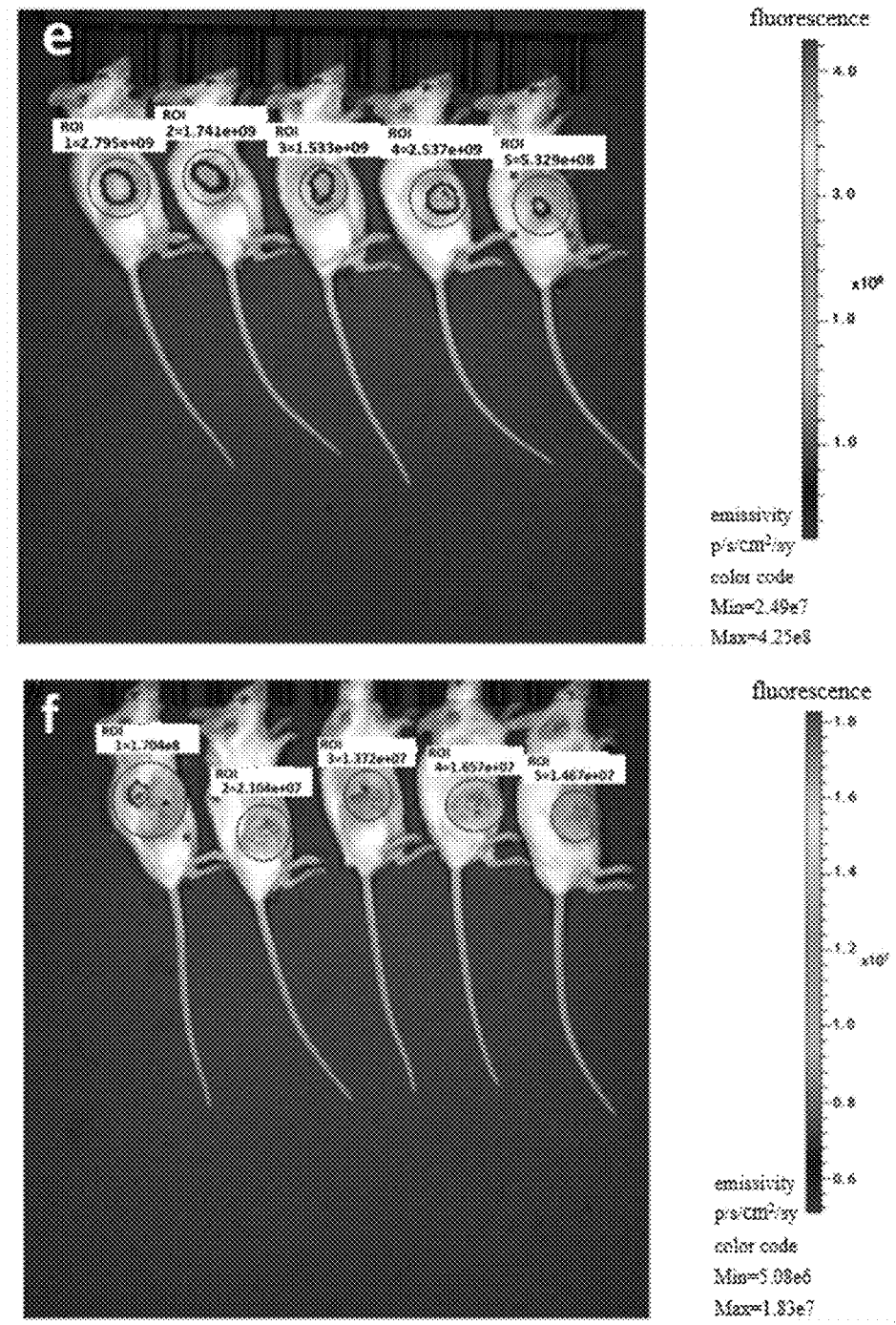
Figure 4:
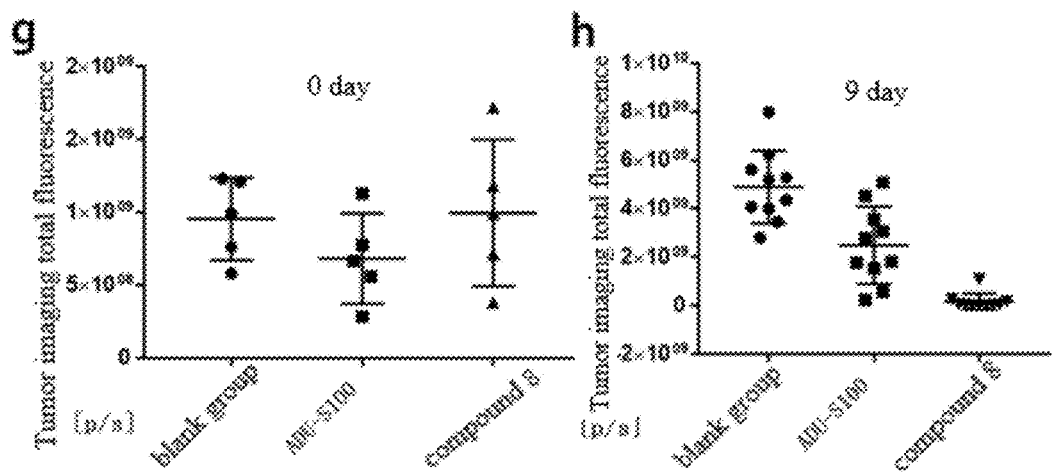
Figure 5:
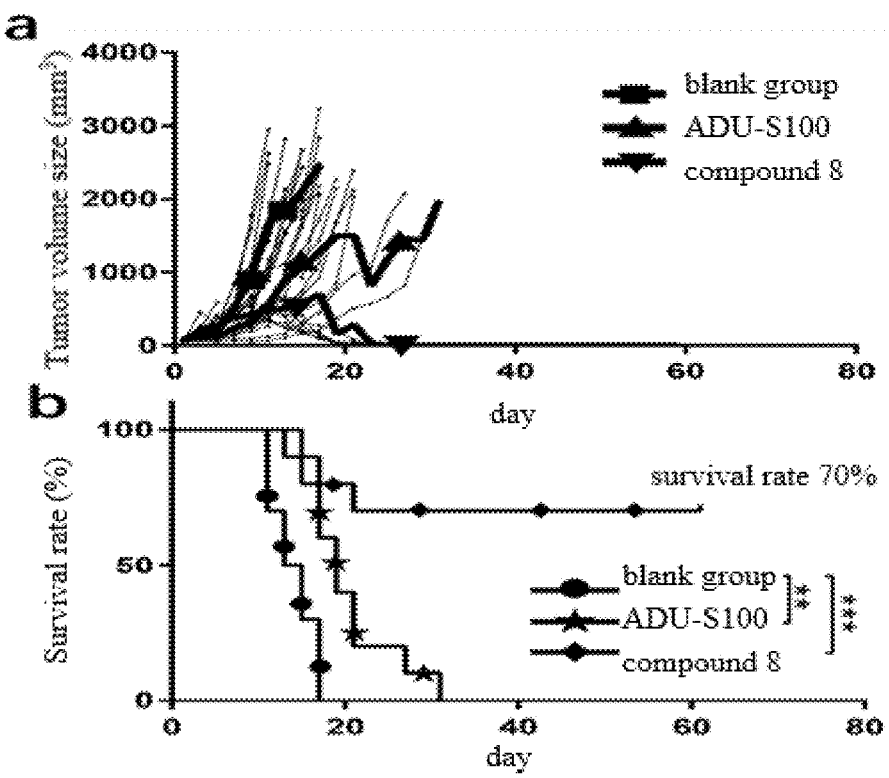

In FIG. 4, a is a graph of imaging of tumors at day 0 after administration of a hollow negative control group mouse in Test Example 4, b is a graph of imaging of tumors at day 0 after administration of an ADU-S100 group mouse in Test Example 4, c is a graph of imaging of tumors at day 0 after administration of a compound 8 group mouse in Test Example 4, d is a graph of imaging of tumors at day 9 after administration of a negative control group mouse in Test Example 4, e is a graph of imaging of tumors at day 9 after administration of an ADU-S100 group mouse in Test Example 4, f is a graph of imaging of tumors at day 9 after administration of a compound 8 group mouse in Test Example, g is a graph of statistics of total fluorescence amounts of tumors at day 0 after administration of each group mouse in Test Example 4, and h is a graph of statistics of total fluorescence amounts of imaging of tumors at day 9 after administration of each group mouse in Test Example 4;

In FIG. 5, a is the size of the tumor volume in the mice of the different experimental groups in Test Example 4, and b is the survival rate of the mice of the different experimental groups in Test Example 4.

DETAILED DESCRIPTION

The endpoints of the ranges and any values disclosed herein are not limited to the precise range or value, and these ranges or values should be understood to encompass values close to these ranges or values. For numerical ranges, each range between its endpoints and individual point values, and each individual point value can be combined with each other to give one or more new numerical ranges, and such numerical ranges should be construed as specifically disclosed herein.

As previously mentioned, in a first aspect, the present invention provided a cyclic dinucleotide prodrug molecule, or a stereoisomer, a tautomer, a nitrogen oxide, a solvate, a metabolite, a pharmaceutically acceptable salt thereof.

The inventor of the present invention unexpectedly found in the research that by introducing a phosphate ester protecting group containing a thioester structure and/or a disulfide bond structure as shown in $Y_1$ and/or $Y_2$ into a cyclic dinucleotide molecule to form a phosphotriester cyclic dinucleotide prodrug molecule, the influence of negative charges of phosphate can be eliminated, the protecting group can be removed in cytoplasm, and the cyclic dinucleotide molecule with biological activity can be released, thereby overcoming the defect that the cyclic dinucleotide is difficult to be effectively taken up by cells.

In the present invention, the "aliphatic hydrocarbon groups of $C_1$-$C_{10}$" represents an alkyl group or alkenyl group having a total number of carbon atoms of 1 to 10, and may be, for example, a methyl group, an ethyl group, an n-propyl group, an isopropyl group, an n-butyl group, a sec-butyl group, an isobutyl group, a tert-butyl group, an n-pentyl group, an isopentyl group, a tert-pentyl group, a neopentyl group, an n-hexyl group, an isohexyl group, an n-heptyl group, an isoheptyl group, an n-octyl group, an isooctyl group, an ethenyl group, an propenyl group or the like.

The "aliphatic hydrocarbon groups of $C_1$-$C_6$" represents an alkyl group or an alkenyl group having a total number of carbon atoms of 1 to 6, and may be, for example, a methyl group, an ethyl group, an n-propyl group, an isopropyl group, an n-butyl group, a sec-butyl group, an isobutyl group, a tert-butyl group, an n-pentyl group, an isopentyl group, a tert-pentyl group, a neopentyl group, an n-hexyl group, an isohexyl group, an ethenyl group, a propenyl group or the like.

The "aromatic hydrocarbon groups of $C_6$-$C_{11}$" represents an aromatic ring having one or more hydrogen atoms removed, and includes an aromatic ring to which other functional groups or substituents are bonded, and may be, for example,

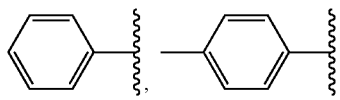

or the like.

In the present invention, the five-membered or six-membered heterocyclic groups represents saturated or unsaturated five-membered heterocyclic groups, or saturated or unsaturated six-membered heterocyclic groups, and may be, for example,

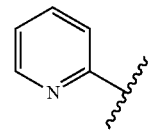 [SMILES: *c1ccccn1]

or the like.

In the present invention, the "$C_1$-$C_5$ alkylgroups" represents an alkyl group having a total number of carbon atoms of 1 to 5, and may be, for example, a methyl group, an ethyl group, an n-propyl group, an isopropyl group, an n-butyl group, a sec-butyl group, an isobutyl group, a tert-butyl group, an n-pentyl group, an isopentyl group, a tert-pentyl group, or a neopentyl group.

In the present invention, the "$C_1$-$C_5$ alkoxy groups" represents an alkoxy group having a total number of carbon atoms of 1 to 5, and may be, for example, a methoxy group, anethoxy group, a propoxy group, a butoxy group, a pentoxy group or the like.

In the present invention, the halogen may be fluorine, chlorine, bromine, iodine.

Preferably, $R_1$, $R_2$, $R_3$ and $R_4$ are each independently selected from substituted or unsubstituted aliphatic hydrocarbon groups of $C_1$-$C_6$, substituted or unsubstituted aromatic hydrocarbon groups of $C_6$-$C_{11}$, five-membered or six-membered heterocyclic groups; and the substituents optionally present in $R_1$, $R_2$, $R_3$ and $R_4$ are each independently selected from the group consisting of $C_1$-$C_5$ alkyl groups, $C_1$-$C_5$ alkoxy groups and halogen.

According to a preferred embodiment, in the structures of formula I, formula II or formula III, $Y_1$ and $Y_2$ are the same; $B_1$ is the same as $B_2$; $X_1$ is the same as $X_2$.

According to another preferred embodiment, $n_1$, $n_2$, $n_3$ and $n_4$ in $Y_1$ and $Y_2$ are the same and are integers from 1 to 3.

According to another preferred embodiment, the cyclic dinucleotide prodrug molecule has any one of structures represented by formula (1) to formula (10):

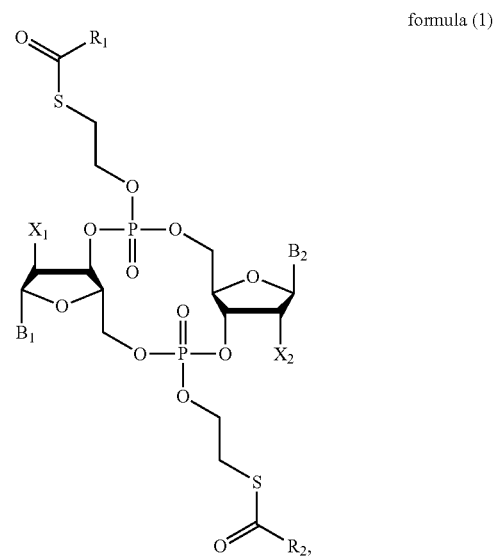

formula (1)

formula (2)
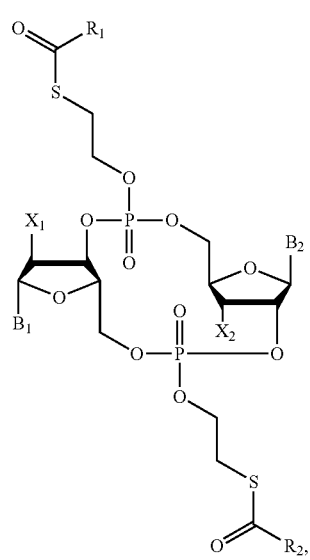
formula (3)
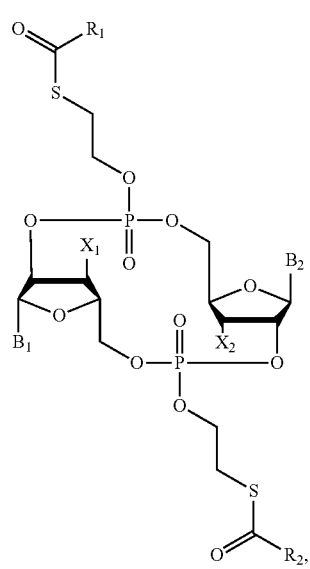
formula (4)
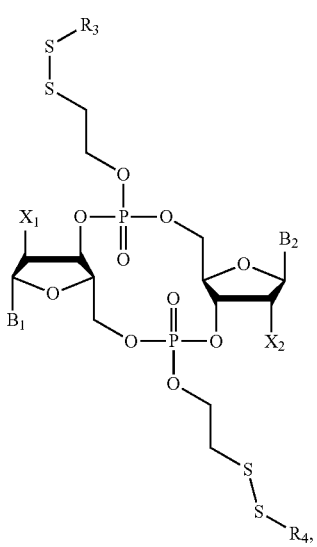
formula (5)
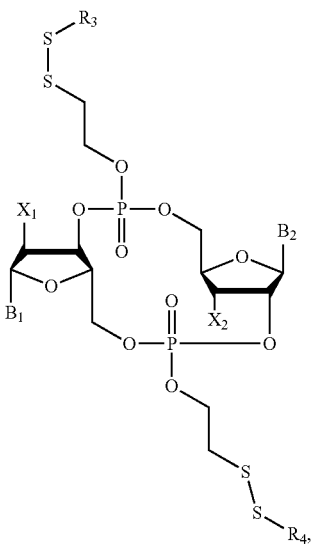
formula (6)
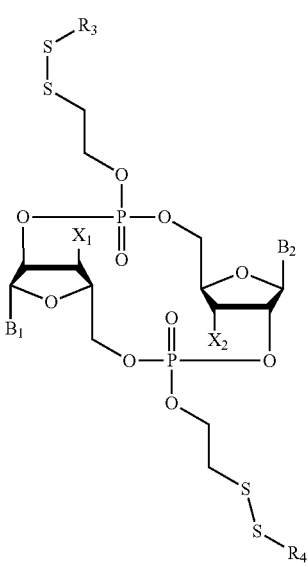
formula (7)
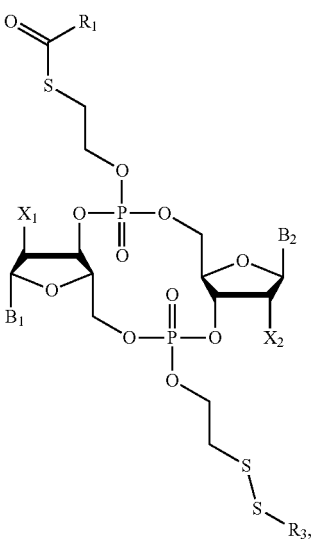

9
-continued

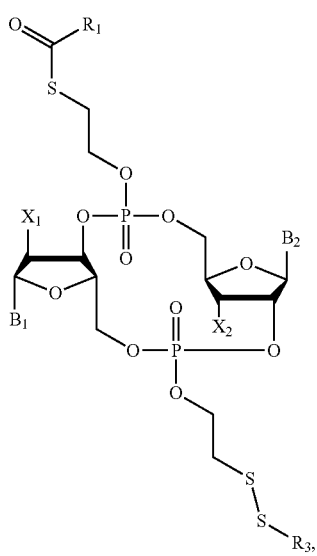

formula (8)

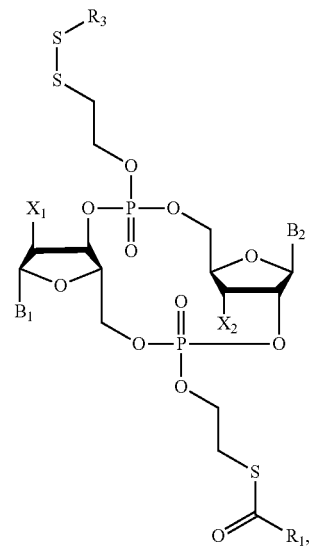

formula (9)

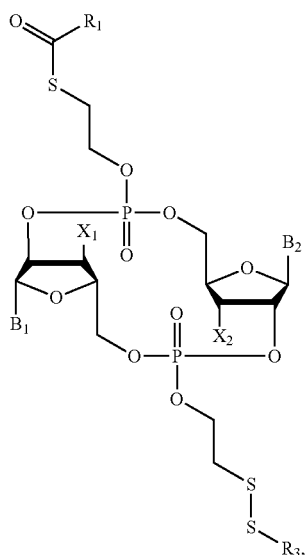

formula (10)

10 wherein the definitions of the groups in the formula (1) to formula (10) correspond to the same definitions as described herein before.

Particularly preferably, the cyclic dinucleotide prodrug molecule has any one of structures shown in formula (1) to formula (10), and in formula (1) to formula (10), $B_1$ is the same as $B_2$ and is selected from the group consisting of guanine, adenine, cytosine, thymine and uracil;

both $X_1$ and $X_2$ are —H;

$R_1$, $R_2$, $R_3$ and $R_4$ are the same and are selected from substituted or unsubstituted aliphatic hydrocarbon groups of $C_1$-$C_6$, substituted or unsubstituted aromatic hydrocarbon groups of $C_6$-$C_{11}$ and five-membered or six-membered heterocyclic groups; and the substituents optionally present in $R_1$, $R_2$, $R_3$ and $R_4$ are selected from $C_1$-$C_5$ alkyl groups.

The present invention provides a preferred embodiment, wherein the cyclic dinucleotide has a structure represented by formula (11),

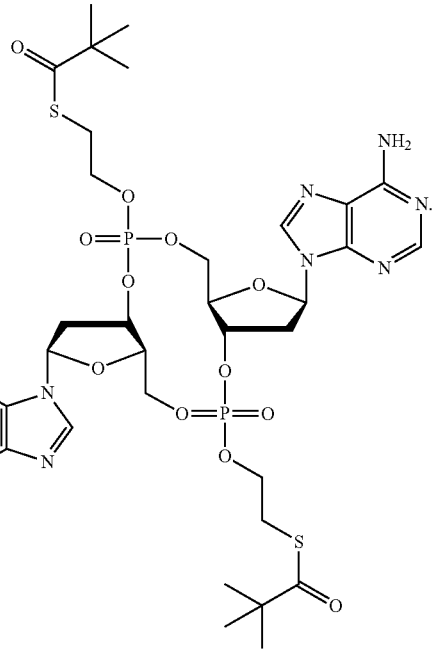

formula (11)

According to another preferred embodiment of the present invention, the cyclic dinucleotide has a structure represented by formula (12), formula (12)

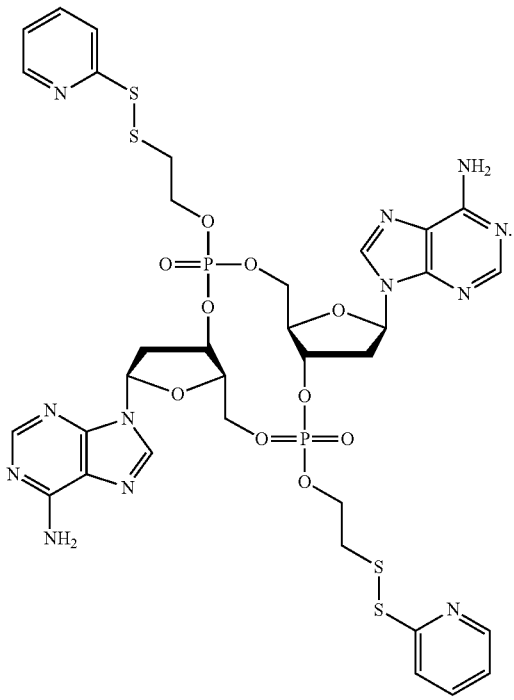

As previously mentioned, a second aspect of the invention provided a method of preparing the cyclic dinucleotide prodrug molecule of the invention.

The protecting group used in the preparation of the cyclic dinucleotide prodrug molecules according to the present invention is an acyl group, which may be, for example, a benzoyl group, an isobutyryl group, an acetyl group, a phenoxyacetyl group, a 4-isopropylphenoxyacetyl group or the like.

Particularly preferably, the protecting group is selected from phenoxyacetyl or 4-isopropylphenoxyacetyl.

Formula (13) and formula (14), DMTr-is 4, 4'-dimethoxytriphenylmethyl.

In the present invention, the amount of each substance used in the method is not particularly limited, and can be selected by those skilled in the art according to the needs of each reaction.

Preferably, the conditions for carrying out the first contact reaction include: the temperature is 0° C. to 50° C. and the time is 2 h to 8 h.

Preferably, the conditions for carrying out the second contact reaction include: the temperature is 0° C. to 50° C. and the time is 2 h to 8 h.

Preferably, the first condensing agent and the second condensing agent are each independently selected from at least one of 1-(mesitylene-2-sulfone)-3-nitro-1, 2, 4-triazole, 2,4, 6-triisopropylphenylsulfone-3-nitro-1, 2, 4-triazole, 2,4, 6-triisopropylbenzenesulfonyl chloride, 2,4, 6-trimethylbenzenesulfonyl chloride, 1H-tetrazole, and N-methylimidazole.

In the present invention, the first liquid reaction medium and the second liquid reaction medium are reaction media commonly used in the art, and for example, pyridine, dichloromethane, acetonitrile, dioxane, tetrahydrofuran, etc. can be used, and those skilled in the art can select them according to the type of reaction.

Preferably, in the step a), the first condensing agent is used in an amount of 2 mol to 3 mol with respect to 1 mol of the first nucleotide monomer compound.

Preferably, in the step b), the second condensing agent is used in an amount of 4 mol to 5 mol with respect to 1 mol of the linear dinucleotide intermediate.

In the step b), the alkaline conditions can be provided by, for example, triethylamine, tert-butylamine, diethylamine, diisopropylamine, etc., and particularly preferably, in order to obtain a higher yield of the target product, the alkaline conditions are provided by a solution of tert-butylamine in acetonitrile. Particularly preferably, the alkaline conditions are provided by a mixed solution of tert-butylamine and acetonitrile in a volume ratio of 1:(1 to 5).

Preferably, the deprotection group is reacted in the presence of a mixed solution of diisopropylamine and methanol in a volume ratio of 1:(5 to 20).

According to a preferred embodiment of the present invention, the method of preparing the cyclic dinucleotide prodrug molecule of the present invention includes:

1) adding the first nucleotide monomer compound, the second nucleotide monomer compound and 1-(mesitylene-2-sulfone)-3-nitro-1, 2, 4-triazole into pyridine, and reacting for 2 h to 8 h at 0° C. to 50° C. in an inert gas atmosphere to obtain a linear dinucleotide intermediate;

2) adding the linear dinucleotide intermediate obtained in the step 1) into a mixed solution of tert-butylamine and acetonitrile to react for 10 min to 30 min, evaporating the solvent to dryness, adding 1-(mesitylene-2-sulfone)-3-nitro-1, 2, 4-triazole, dissolving with pyridine, and reacting at 0° C. to 50° C. for 2 h to 8 h to obtain a cyclic dinucleotide prodrug molecule with a protecting group; in the mixed solution of the tert-butylamine and the acetonitrile, the volume ratio of the tert-butylamine to the acetonitrile is 1:(1 to 5);

3) dissolving the cyclic dinucleotide prodrug molecule with the protecting group into a mixed solution of diisopropylamine and methanol, and reacting at the temperature of 20° C. to 30° C. for 3 h to 5 h to obtain the cyclic dinucleotide prodrug molecule; in the mixed solution of diisopropylamine and methanol, the volume ratio of diisopropylamine to methanol is 1:(5 to 20).

In the present invention, the synthesis of the first nucleotide monomer compound and the second nucleotide monomer compound may be a method commonly used in the art, and those skilled in the art may design a synthetic route by himself or herself based on the structures represented by formula (13) to formula (16) provided in the present invention. The invention herein illustratively provides several specific synthetic methods:
the first method includes the following steps:

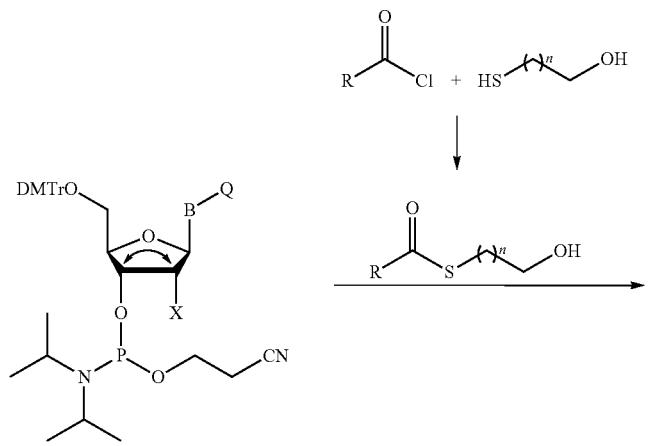

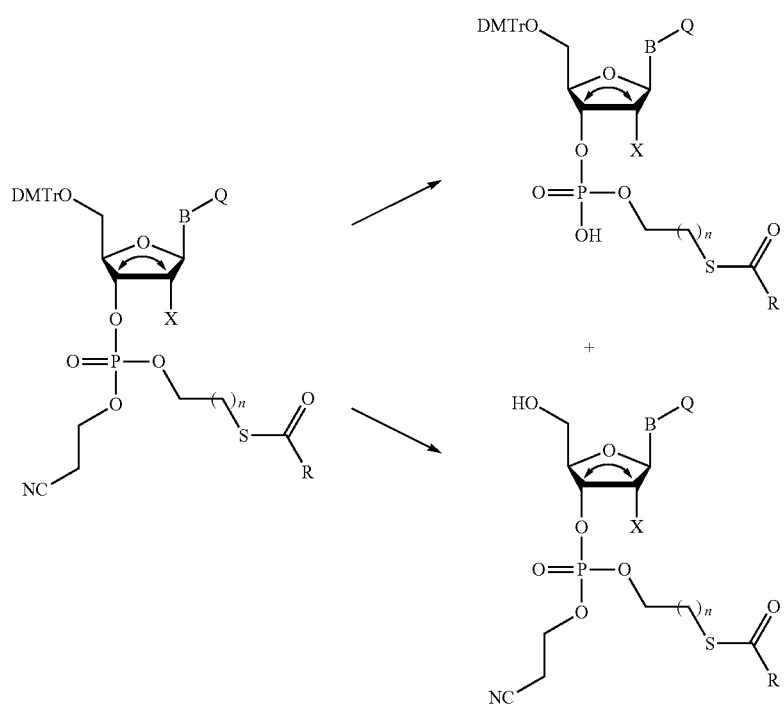

In the first method, R may be $R_1$ or $R_2$, B may be $B_1$ or $B_2$, X may be $X_1$ or $X_2$, and n may be $n_1$ or $n_2$. The method includes the following steps:
  (i) dissolving sulfhydryl substituted alcohol and triethylamine in dichloromethane, dripping dichloromethane solution of acyl chloride at (−80° C.) to (−70° C.), heating to 20° C. to 30° C., reacting for 1 h to 3 h, adding water for quenching, extracting by using an organic solvent, and performing column chromatography separation to obtain thioester substituted alcohol;
  (ii) adding a nucleoside phosphoramidite monomer, 5-(ethyltion)-1H-tetrazole and thioester substituted alcohol obtained in the step (i) into anhydrous acetonitrile, reacting for 1 h to 3 h in an inert gas atmosphere, adding tert-butylhydroperoxide, adding a sodium sulfite aqueous solution for quenching after 30 min to 60 min, extracting with an organic solvent, and performing column chromatography separation to obtain a nucleotide monomer with thioester protecting group;
  (iii) dissolving the nucleotide monomer with thioester protecting group obtained in the step (ii) with dichloromethane, adding dichloroacetic acid, reacting at 20° C. to 30° C. for 1 h to 3 h, and performing column chromatography to obtain the first nucleotide monomer compound;
  (iv) dissolving the nucleotide monomer with the thioester protecting group obtained in the step (ii) with acetonitrile, adding tert-butylamine, reacting at 20° C. to 30° C. for 1 h to 3 h, and then drying the solvent to obtain the second nucleotide monomer compound.

The second method includes the following steps:

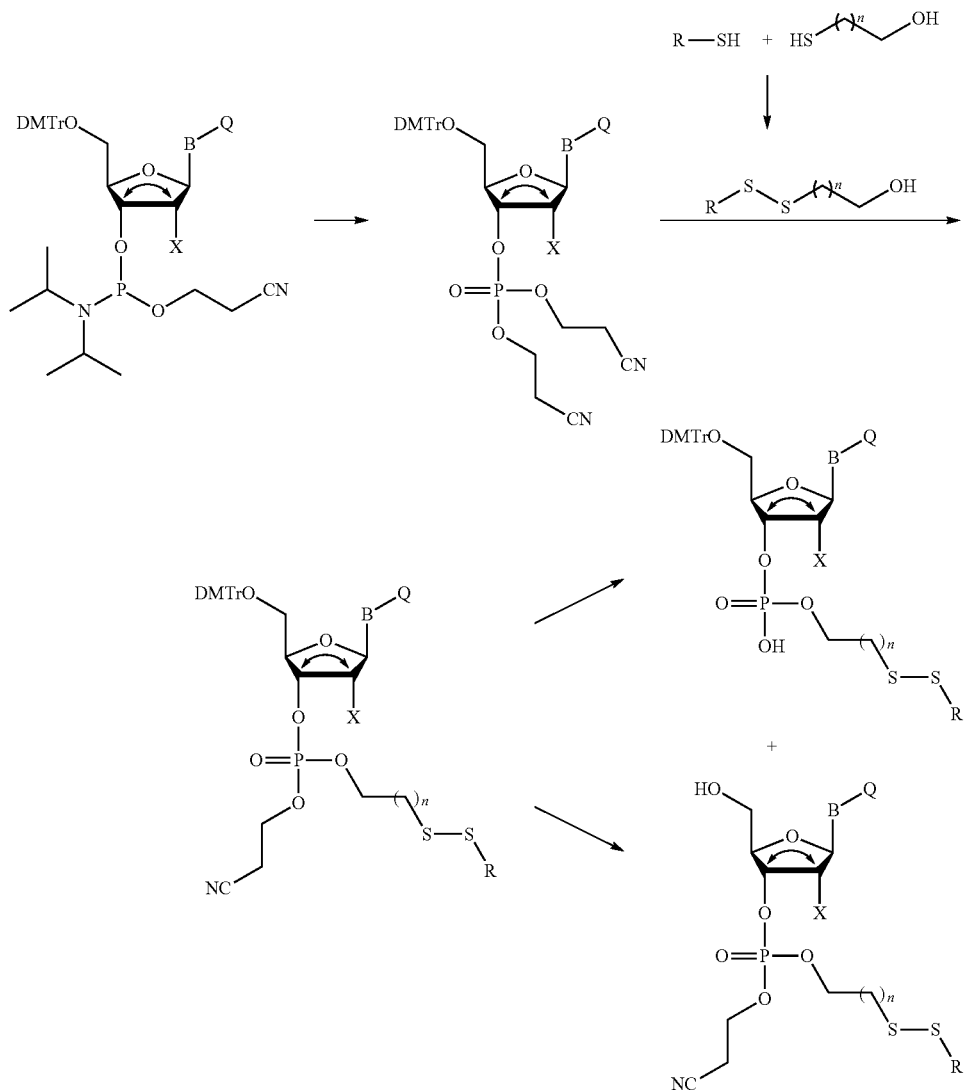

In the second method, R can be $R_3$ or $R_4$, B can be $B_1$ or $B_2$, X can be $X_1$ or $X_2$, and n can be $n_3$ or $n_4$. The second method includes the following steps:
(i) adding N-chlorosuccinimide acyl chloride and mercaptan (or thiophenol) into dichloromethane, reacting at 10° C. to 35° C. for 1 h to 3 h, adding mercapto substituted alcohol, continuing to react for 20 h to 30 h, adding water for quenching, extracting with an organic solvent, and performing column chromatography separation to obtain alcohol containing disulfide bond structure substitution;
(ii) adding 3-hydroxypropionitrile, nucleoside phosphoramidite monomer and 5-(ethyltion)-1H-tetrazole into anhydrous acetonitrile, reacting for 1 h to 3 h in an inert gas atmosphere, adding tert-butylhydroperoxide, continuing to react for 30 min to 60 min, adding sodium bisulfite aqueous solution for quenching, extracting with an organic solvent, and performing column chromatography separation to obtain a dicyanoethyl protected nucleotide monomer;
(iii) dissolving the dicyanoethyl protected nucleotide monomer obtained in the step (ii) with dichloromethane, adding tert-butylamine, stirring at 20° C. to 30° C. for 10 min to 30 min, then, spin-drying the solvent, adding 1-(mesitylene-2-sulfone)-3-nitro-1, 2, 4-triazole and alcohol containing disulfide bond structure substitution obtained in the step (i), dissolving anhydrous pyridine, reacting for 4 h under the protection of inert gas, evaporating the solvent, extracting with an organic solvent, and performing column chromatography separation to obtain the nucleotide monomer with disulfide bond substituted alcohol protected phosphate ester;
(iv) dissolving the nucleotide monomer with disulfide bond substituted alcohol protected phosphate ester obtained in the step (iii) with dichloromethane, adding dichloroacetic acid, reacting at 20° C. to 30° C. for 1 h to 3 h, and performing column chromatography separation to obtain the first nucleotide monomer compound;
(v) dissolving the nucleotide monomer with disulfide bond substituted alcohol protected phosphate ester obtained in the step (iii) with acetonitrile, adding tert-butylamine, stirring at 20° C. to 30° C. for 10 min to 30 min, and then spin-drying the solvent to obtain the second nucleotide monomer compound.

In the first method and the second method, the amount of each substance used is not particularly limited, and can be selected by those skilled in the art according to the needs of the reaction.

In a third aspect, the present invention provided the cyclic dinucleotide prodrug molecule of the present invention, or a stereoisomer, a tautomer, a nitrogen oxide, a solvate, a metabolite, a pharmaceutically acceptable salt thereof, for the preparation of a drug.

Preferably, the drug is an antiviral drug, an antibacterial infection drug or an anticancer drug.

The cyclic dinucleotide prodrug molecule can independently cross cell membranes and release the cyclic dinucleotide, the released cyclic dinucleotide can be combined with a stimulator of interferon genes (STING) to stimulate an immune response, and the cyclic dinucleotide prodrug molecule can be applied to preparation of antiviral drug, antibacterial infection drug and anticancer drug.

The reaction according to the second aspect of the present invention may be carried out by any of various post-treatment methods conventionally used in the art.

Methods of such post-processing include, but are not limited to: extraction, recrystallization, washing, drying, filtration and the like. The present invention is not described in detail herein, and the post-processing methods mentioned in the embodiments are only used for exemplary enumeration and do not indicate that they are necessary operations, and those skilled in the art can substitute conventional other means.

The present invention will be described in detail below by way of examples.

In the following examples, the solvents, starting materials and reagents used are all commercially available, either analytically pure or chemically pure, unless otherwise specified.

The anhydrous solvents required for the experiments were dried by conventional methods.

The product separation and identification device and method are as follows:

the thin layer chromatography silica gel GF254 is produced by Tianjin Silida company.

TLC analysis is under UV light at 254 nm, and column chromatography silica gel is produced by Qingdao ocean chemical company.

The nuclear magnetic resonance spectrometer was obtained by Bruker AVANCE 400M Hz, TMS as internal standard.

The high-resolution mass spectrum was obtained by Varian 7.0T FTMS Fourier transform plasma cyclotron resonance high-resolution mass spectrum.

The normal temperature and the room temperature are both (25±3° C.)

Example 1

Synthesis of cyclic dinucleotide prodrug molecules with pentanoyl thioethyl ester protection (compound 8)

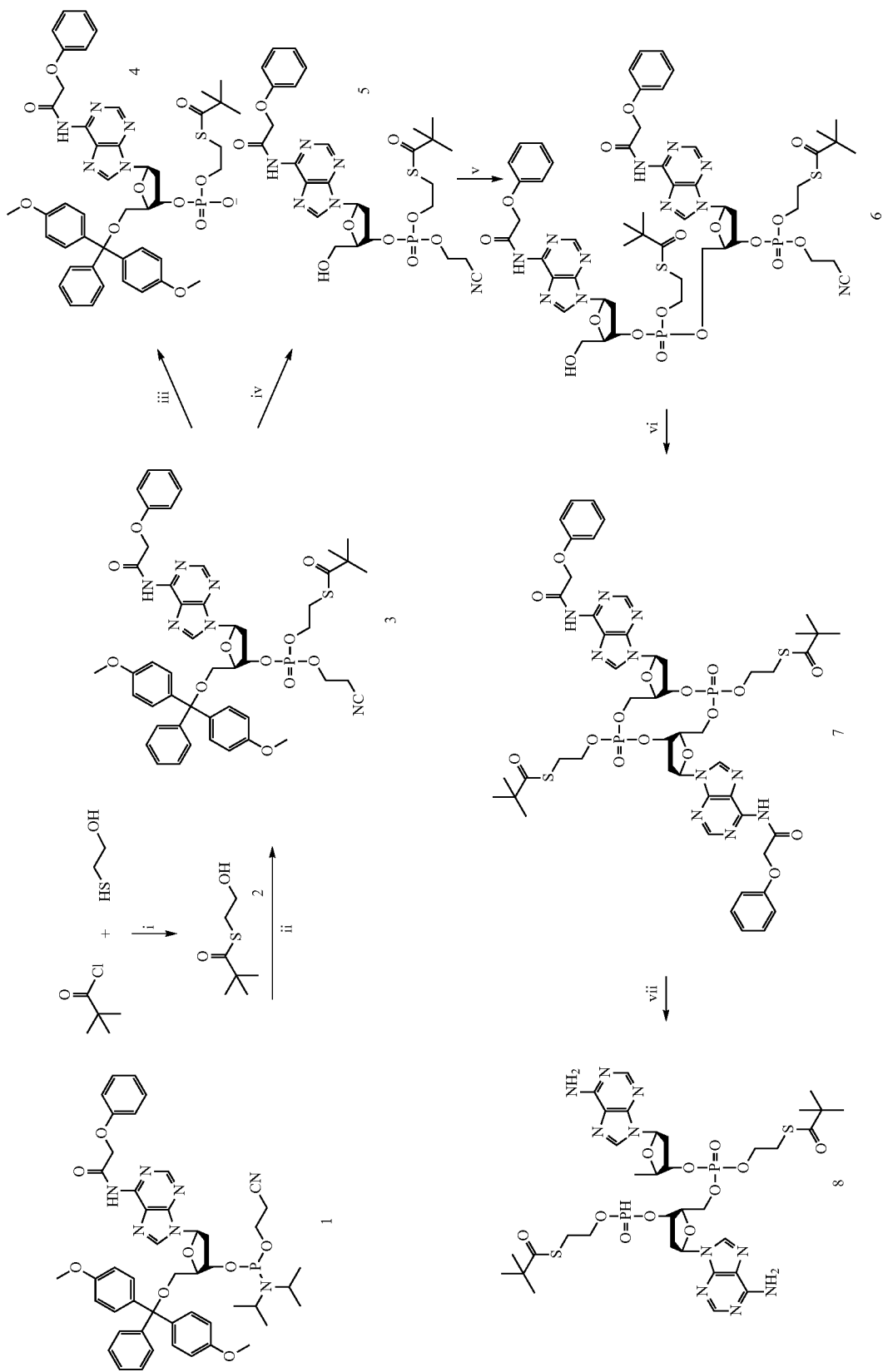

1) In a 100 mL flask, 2-mercaptoethanol 0.9 mL, triethylamine 1.8 mL and 10 mL redistilled dichloromethane were added, pentaeryl chloride (1.6 mL, dissolved in 10 mL dichloromethane) was added dropwise at −78° C. in half an hour. The reaction was continued for 1 h, then slowly warmed to room temperature, and stirring was continued for 1 h. Adding a proper amount of water to quench the reaction, extracting the water phase with dichloromethane twice, combining the organic phases, washing with saturated saline solution, drying with anhydrous sodium sulfate, filtering, concentrating, and separating by column chromatography to obtain the compound 2.

The nuclear magnetic resonance data are:

1H NMR (400 MHz, CDCl3) δ 3.73 (t, J=6.1 Hz, 9H), 3.04 (t, J=6.1 Hz, 9H), 1.23 (s, 41H).

13C NMR (101 MHz in CDCl3) δ 207.36, 61.91, 46.57, 31.49, 27.40.

The data indicate that the compound was synthesized correctly.

2) The compound 2 (1.12 mmol), 5-(ethyltion)-1H-tetrazole (3.36 mmol) and the compound 1 (1.12 mmol) were added into a flask. 10 mL of anhydrous acetonitrile was added and stirring was carried out at room temperature for 1 h, and then 1 mL of 5.5M tert-butylhydroperoxide-decane solution was added. After further stirring at room temperature for 40 min, an aqueous solution of sodium bisulfite solution was added and the mixture was stirred, and after repeated extraction with dichloromethane, the organic phases were combined, washed with saturated saline solution, dried over anhydrous sodium sulfate, filtered, concentrated, and separated by column chromatography to obtain the compound 3 (950 mg).

The nuclear magnetic resonance data are:

1H NMR (400 MHz, CDCl$_3$) δ 9.59 (s, 1H), 8.77 (s, 1H), 8.17 (d, J=7.2 Hz, 1H), 7.46-7.23 (m, 10H), 7.21-7.14 (m, 3H), 7.06 (t, J=8.1 Hz, 3H), 6.89-6.76 (m, 4H), 6.46 (dd, J=9.5, 5.3 Hz, 1H), 5.41-5.31 (m, 1H), 4.88 (s, 2H), 4.49 (d, J=1.3 Hz, 1H), 4.38-4.29 (m, 2H), 4.18 (dd, J=15.0, 6.9 Hz, 2H), 3.99 (dd, J=13.0, 1.3 Hz, 1H), 3.89 (d, J=13.1 Hz, 1H), 3.83-3.71 (m, 7H), 3.18 (t, J=6.9 Hz, 4H), 3.05 (s, 1H), 2.81 (t, J=6.0 Hz, 2H), 2.77-2.66 (m, 1H), 1.29-1.17 (m, 12H).

13C NMR (101 MHz, CDCl$_3$) δ 205.84, 205.76, 166.70, 158.57, 158.37, 156.92, 152.07, 150.57, 149.10, 147.35, 143.09, 139.47, 136.15, 130.04, 129.86, 129.16, 129.13, 128.15, 127.82, 127.76, 127.75, 127.05, 124.07, 122.49, 116.44, 116.39, 114.91, 113.20, 113.12, 113.10, 113.09, 113.01, 87.79, 87.74, 87.40, 81.38, 80.69, 80.66, 77.37, 77.26, 77.05, 76.73, 68.07, 66.69, 66.67, 66.62, 63.04, 62.38, 62.33, 61.89, 55.24, 55.22, 55.19, 46.63, 39.06, 31.50, 30.95, 28.32, 28.28, 28.25, 27.45, 27.39, 27.30, 27.27, 19.84, 19.77.

The data indicate that the compound was synthesized correctly.

3) After the compound 3 (0.5 mmol) was added to the flask and dissolved by adding 10 mL of dichloromethane, 10 mL of 6 vol % dichloroacetic acid-dichloromethane solution was added under ice bath. After reacting for 5 min, adding a small amount of methanol to quench the reaction. Adding saturated aqueous solution of sodium bicarbonate to neutralize, extracting, drying, concentrating, and separating by column chromatography to obtain the compound 5 (330 mg).

The nuclear magnetic resonance data are:

1H NMR (400 MHz, CDCl$_3$) δ 8.78 (s, 1H), 8.24 (d, J=6.1 Hz, 1H), 7.43-7.31 (m, 2H), 7.06 (t, J=8.0 Hz, 3H), 6.48 (dd, J=9.4, 5.3 Hz, 1H), 5.35 (dd, J=8.9, 5.3 Hz, 1H), 4.89 (s, 2H), 4.50 (d, J=1.0 Hz, 1H), 4.44-4.27 (m, 2H), 4.18 (dd, J=15.0, 6.9 Hz, 2H), 3.95 (ddd, J=13.2, 12.1, 1.9 Hz, 2H), 3.18 (t, J=6.8 Hz, 3H), 2.83 (t, J=6.0 Hz, 2H), 2.72 (dt, J=13.9, 5.4 Hz, 1H), 1.25 (s, 10H). [0106]13C NMR (101 MHz, CDCl$_3$) δ 205.88, 205.79, 166.81, 156.94, 152.09, 150.58, 149.05, 143.11, 129.87, 123.91, 122.49, 116.46, 116.41, 114.91, 87.78, 87.73, 87.37, 80.62, 80.59, 77.37, 77.26, 77.06, 76.74, 68.08, 66.71, 66.69, 66.65, 66.63, 63.00, 62.40, 62.35, 61.89, 46.63, 39.14, 39.10, 31.49, 28.35, 28.32, 28.28, 28.25, 27.39, 27.31, 19.87, 19.85, 19.80, 19.78.

The data indicate that the compound was synthesized correctly.

4) In a flask, the compound 3 (0.27 mmol), tert-butylamine/acetonitrile (1:3, v/v) 10 mL were added and stirred at room temperature for 20 min, and then the solvent was removed by rotary evaporation to obtain the compound 4. Adding the compound 2 (0.27 mmol), 1-(mesitylene-2-sulfone)-3-nitro-1, 2, 4-triazole (1.63 mmol) and 10 mL of pyridine stirring at room temperature for 2 h. Adding a small amount of water to quench the reaction, removing the solvent by rotary evaporation, adding 20 mL of dichloromethane to dissolve the solution, adding a proper amount of 5 wt % aqueous solution of oxalic acid, separating out an organic phase, drying, filtering and concentrating the organic phase, adding 3 vol % dichloromethane solution of dichloroacetic acid, stirring for 5 min, adding a proper amount of methanol and saturated aqueous solution of sodium bicarbonate to neutralize the solution, extracting, drying the organic phase, filtering, concentrating and separating by column chromatography to obtain the compound 6 (320 mg).

The nuclear magnetic resonance data are:

1H NMR (400 MHz, CDCl$_3$) δ 9.96-9.72 (m, 2H), 8.66 (dt, J=7.8, 5.3 Hz, 2H), 8.35 (dd, J=13.1, 6.2 Hz, 2H), 7.24 (ddd, J=15.0, 10.1, 2.5 Hz, 5H), 7.05-6.81 (m, 7H), 6.49 (ddd, J=25.0, 17.3, 8.7 Hz, 2H), 5.72 (s, 1H), 5.37 (s, 1H), 5.24 (q, J=5.9 Hz, 2H), 4.90 (s, 4H), 4.51 (s, 1H), 4.46-4.21 (m, 6H), 4.20-3.99 (m, 5H), 3.84 (t, J=14.1 Hz, 2H), 3.09 (ddd, J=52.8, 29.8, 23.2 Hz, 7H), 2.81 (d, J=5.2 Hz, 4H), 2.62 (td, J=13.2, 4.7 Hz, 1H), 1.18 (dt, J=9.7, 6.8 Hz, 22H).

13C NMR (101 MHz, CDCl$_3$) δ 205.70, 205.69, 205.64, 167.56, 157.15, 157.10, 157.06, 152.47, 151.75, 151.44, 151.35, 150.60, 150.56, 148.97, 148.57, 148.55, 143.66, 143.62, 142.44, 129.73, 129.69, 123.57, 123.00, 122.15, 116.76, 116.73, 114.81, 114.77, 114.75, 87.44, 87.40, 86.79, 84.57, 83.67, 80.24, 78.10, 77.85, 77.58, 77.46, 77.26, 76.94, 68.29, 68.17, 66.88, 66.82, 66.61, 66.55, 62.76, 62.63, 62.58, 53.57, 46.56, 46.52, 38.90, 38.05, 37.86, 31.87, 29.64, 29.31, 28.38, 28.34, 28.30, 28.27, 28.20, 27.41, 27.25, 22.65, 19.79, 19.72, 14.14.

The data indicate that the compound was synthesized correctly.

5) The compound 6 (0.22 mmol) was added to tert-butylamine/acetonitrile (1:3, v/v) of the reaction solution, stirring at room temperature for 20 min, removing the solvent by rotary evaporation, adding 100 mL of pyridine for dissolution, adding 1-(mesitylene-2-sulfone)-3-nitro-1, 2, 4-triazole (1.35 mmol), reacting at room temperature for 4 h, removing the solvent, adding 20 mL of dichloromethane for dissolution, adding a proper amount of 5 wt % aqueous solution of oxalic acid, separating out the organic phase, drying, filtering, concentrating, and separating by column chromatography to obtain the compound 7 (160 mg).

The nuclear magnetic resonance data are:

1H NMR (400 MHz, CDCl$_3$) δ 9.69 (s, 2H), 8.80 (d, J=3.2 Hz, 2H), 8.43-8.15 (m, 2H), 7.30 (td, J=15.8, 8.5 Hz, 7H), 7.14-6.85 (m, 9H), 6.49 (ddd, J=17.3, 11.7, 5.4 Hz, 2H), 5.67-5.33 (m, 2H), 4.91 (s, 4H), 4.78 (s, 1H), 4.65 (d, J=4.9 Hz, 1H), 4.61-4.30 (m, 6H), 4.26-4.05 (m, 6H), 3.67-3.36 (m, 2H), 3.16 (dt, J=9.8, 7.1 Hz, 5H), 2.78 (td, J=14.4, 5.6 Hz, 2H), 1.27-1.17 (m, 23H).

13C NMR (101 MHz, CDCl$_3$) δ 205.76, 205.74, 205.60, 205.53, 172.28, 167.03, 157.76, 157.05, 157.02, 156.60, 152.63, 152.57, 152.48, 152.38, 152.23, 151.49, 151.41, 151.31, 151.20, 148.70, 148.66, 148.58, 143.05, 142.75, 142.55, 142.32, 129.95, 129.81, 129.58, 129.54, 123.57, 123.44, 122.75, 122.38, 122.35, 122.33, 121.78, 121.58, 114.88, 114.77, 114.57, 114.55, 85.60, 85.18, 83.04, 82.55, 78.87, 77.30, 77.10, 76.78, 68.12, 67.19, 67.02, 66.96, 66.92, 66.88, 66.83, 66.74, 65.38, 65.24, 65.10, 52.28, 46.59, 46.56, 36.60, 36.34, 31.90, 29.67, 29.64, 29.34, 28.43, 28.36, 28.29, 28.22, 28.16, 27.29, 27.24, 27.23, 22.68, 14.13.

The data indicate that the compound was synthesized correctly.

6) The compound 7 (150 mg) was added into a flask, and 5 mL of methanol was added to dissolve it, 500 μL of diisopropylamine was added thereto, and stirred at room temperature for 4 h, and the solvent was dried by spin drying, followed by direct column chromatography to separate the compound 8 (80 mg).

The nuclear magnetic resonance data are:

1H NMR (400 MHz, CDCl$_3$) δ 8.33 (d, J=8.4 Hz, 2H), 7.94 (d, J=8.1 Hz, 2H), 6.41 (dd, J=13.9, 7.4 Hz, 2H), 6.20 (d, J=30.1 Hz, 4H), 5.45 (d, J=59.0 Hz, 2H), 4.51 (dd, J=16.6, 8.1 Hz, 3H), 4.39 (t, J=8.3 Hz, 2H), 4.16 (tt, J=9.5, 4.9 Hz, 5H), 3.17 (dd, J=11.4, 6.6 Hz, 4H), 2.82-2.66 (m, 2H), 2.26 (s, 6H), 1.22 (d, J=13.3 Hz, 18H).

13C NMR (101 MHz, CDCl$_3$) δ 205.98, 205.90, 155.69, 155.61, 152.81, 149.41, 149.31, 139.68, 139.53, 120.21, 120.08, 85.29, 82.93, 82.55, 79.07, 77.91, 77.49, 77.38, 77.17, 76.85, 67.12, 67.05, 67.00, 65.48, 65.09, 50.41, 46.67, 46.63, 36.67, 36.61, 28.51, 28.44, 28.35, 28.28, 27.31, 27.27.

MALDI-TOF-HRMS: the relative molecular mass of $C_{34}H_{50}N_{10}O_{11}P_2S_2$ was 900.2577, and a peak of [M+H]$^+$ 901.2654 was found.

The data indicate that the compound was synthesized correctly.

Example 2

Synthesis of Cyclic Dinucleotide Prodrug Molecules with Pyridyldithio Substituted Ethyl Ester Protection (Compound 16)

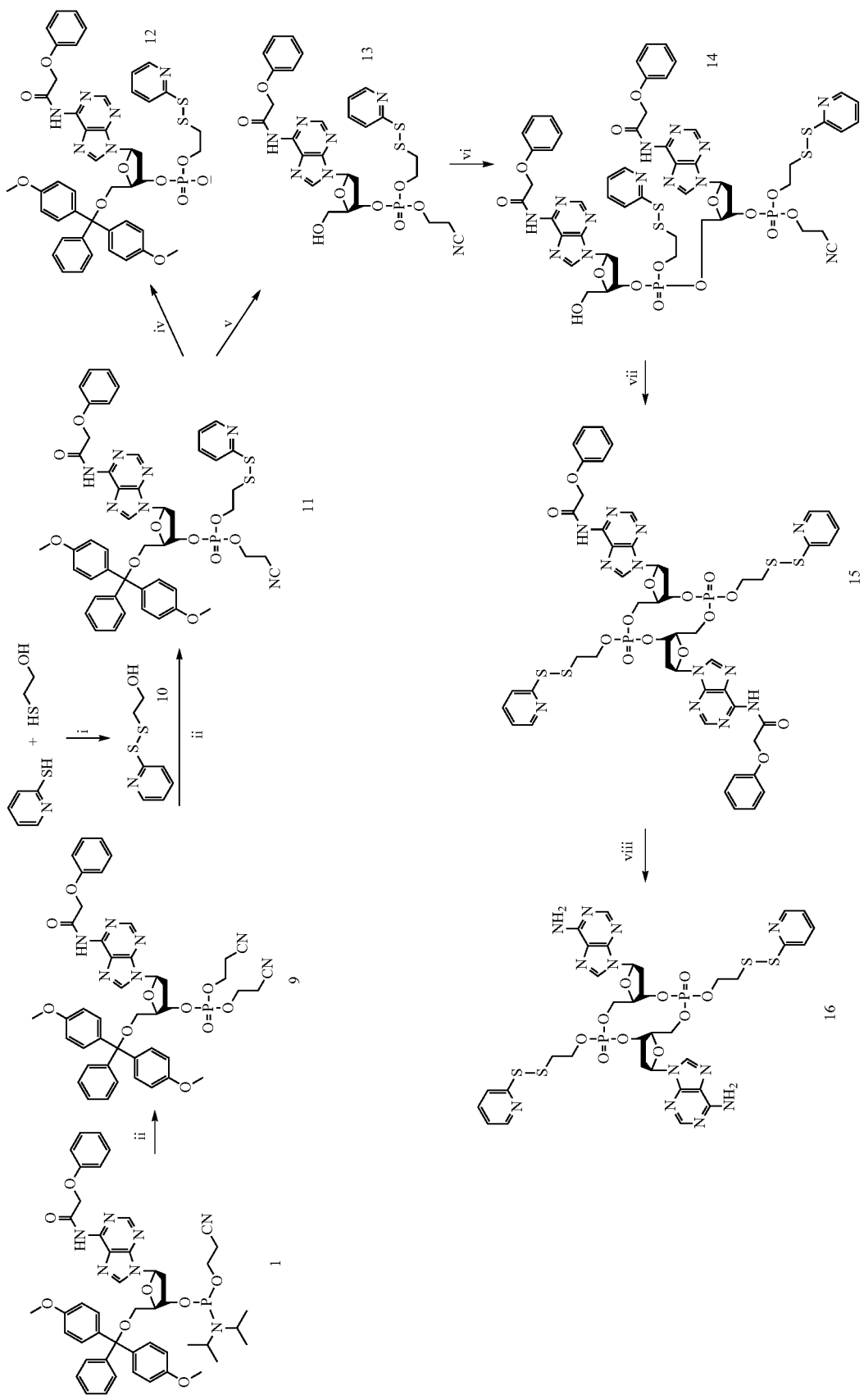

1) Adding 3.42 g of N-chlorosuccinimide into a flask, adding 10 mL of dry dichloromethane, dropwise adding 2.85 g of 2-mercaptopyridine (dissolved in 5 mL of dichloromethane) under ice bath, continuing to stir at low temperature for 1 h after half an hour, dissolving 2 g of 2-mercaptoethanol in 5 mL of dichloromethane, dropwise adding into the flask under ice bath, and stirring at room temperature for 24 h after dropwise adding. And after the reaction is finished, quickly separating by column chromatography to obtain the compound 10.

The nuclear magnetic resonance data are:

1H NMR (400 MHz, DMSO) δ 9.32 (s, 2H), 8.52 (d, J=4.6 Hz, 1H), 8.00-7.89 (m, 2H), 7.39-7.30 (m, 1H), 3.63 (t, J=6.2 Hz, 2H), 2.96 (t, J=6.2 Hz, 2H).

13C NMR (101 MHz, DMSO) δ 159.40, 148.84, 139.51, 122.01, 120.57, 59.48, 41.77.

The data indicate that the compound was synthesized correctly.

2) The compound 1 (1.68 mmol), 5-(ethyltion)-1H-tetrazole (5.07 mmol), 3-hydroxypropionitrile (1.68 mmol), and 15 mL of acetonitrile were added to a flask, and after stirring at room temperature for 1 h, 1 mL of 5.5M tert-butylhydroperoxide-decane solution was added, and after further stirring at room temperature for 40 min, an appropriate amount of aqueous sodium bisulfite solution was added. Dichloromethane was extracted several times, the organic phases were combined and washed with saturated saline solution, dried over anhydrous sodium sulfate, filtered, concentrated, and separated by column chromatography to obtain the compound 9 (1.27 g).

The nuclear magnetic resonance data are:

1H NMR (400 MHz, CDCl$_3$) δ 8.71 (dd, J=31.2, 1.2 Hz, 1H), 8.21-8.10 (m, 1H), 8.01 (d, J=7.2 Hz, 2H), 7.60 (t, J=7.4 Hz, 1H), 7.50 (t, J=7.5 Hz, 2H), 7.37 (d, J=7.1 Hz, 1H), 7.26 (dd, J=5.9, 2.4 Hz, 6H), 7.16 (d, J=8.7 Hz, 2H), 6.87-6.75 (m, 4H), 6.57-6.37 (m, 1H), 5.36 (dd, J=19.5, 14.0 Hz, 1H), 4.46 (d, J=18.9 Hz, 1H), 4.41-4.21 (m, 4H), 3.93 (dd, J=43.4, 12.6 Hz, 1H), 3.78 (d, J=5.7 Hz, 6H), 3.53-3.37 (m, 1H), 3.18 (ddd, J=15.2, 13.1, 8.8 Hz, 1H), 2.82 (t, J=5.8 Hz, 3H), 2.79-2.65 (m, 2H).

13C NMR (101 MHz, CDCl$_3$) δ 164.63, 158.60, 152.16, 150.59, 150.26, 147.39, 142.67, 139.51, 133.32, 133.01, 130.08, 130.03, 129.15, 128.93, 128.11, 127.96, 127.84, 127.79, 127.06, 113.26, 113.14, 87.64, 87.24, 81.05, 77.38, 77.26, 77.06, 76.74, 62.92, 62.76, 62.70, 62.65, 55.26, 39.05, 19.88, 19.81.

The data indicate that the compound was synthesized correctly.

3) The compound 9 (1.37 mmol) was dissolved in 20 mL of acetonitrile, 5 mL of tert-butylamine was added, and the mixture was stirred at room temperature for 20 min and then dried by spinning. The compound 10 (1.38 mmol), 1-(mesitylene-2-sulfone)-3-nitro-1, 2, 4-triazole (6.86 mmol) and 20 mL of pyridine were added and dissolved, and the mixture was stirred at room temperature for 2 h. Adding a proper amount of water to quench the reaction, removing most of the solvent by rotary evaporation, adding 30 mL of dichloromethane to dissolve the solvent again, adjusting the pH value to 3 by using 5 wt % of oxalic acid aqueous solution, separating an organic phase, washing the organic phase by using saturated saline solution, and drying the organic phase by using anhydrous sodium sulfate.

Filtering, concentrating, and separating by column chromatography to obtain the compound 11 (1.05 g).

The nuclear magnetic resonance data are:

1H NMR (400 MHz, CDCl$_3$) δ 9.57 (d, J=50.7 Hz, 1H), 8.78 (s, 1H), 8.69 (s, 1H), 8.52-8.44 (m, 1H), 8.18 (dd, J=13.4, 3.1 Hz, 1H), 8.04 (s, 1H), 7.71-7.61 (m, 2H), 7.42-7.33 (m, 4H), 7.32-7.23 (m, 6H), 7.21-7.17 (m, 2H), 7.11-7.02 (m, 4H), 6.92-6.76 (m, 4H), 6.54-6.40 (m, 1H), 5.41-5.26 (m, 1H), 4.89 (d, J=5.5 Hz, 2H), 4.54-4.18 (m, 5H), 3.99 (d, J=12.9 Hz, 1H), 3.88 (d, J=12.9 Hz, 1H), 3.84 (s, 1H), 3.82-3.76 (m, 5H), 3.46 (dd, J=17.1, 3.0 Hz, 1H), 3.25-3.01 (m, 3H), 2.88-2.63 (m, 3H).

13C NMR (101 MHz, CDCl$_3$) δ 159.66, 158.82, 158.79, 158.59, 158.55, 156.94, 152.03, 150.57, 149.80, 149.09, 147.36, 146.87, 144.23, 143.14, 141.13, 139.48, 137.32, 135.27, 132.51, 131.39, 130.03, 130.00, 129.85, 129.52, 129.13, 128.70, 128.32, 128.07, 127.92, 127.81, 127.76, 127.03, 124.06, 122.46, 121.26, 121.16, 120.23, 116.47, 116.43, 114.92, 114.90, 113.55, 113.20, 113.13, 113.12, 113.10, 113.08, 113.00, 87.75, 87.69, 87.28, 81.36, 80.69, 80.09, 77.39, 77.27, 77.07, 76.75, 68.09, 65.92, 65.87, 65.83, 62.99, 62.45, 62.40, 55.36, 55.24, 39.07, 38.23, 38.16, 19.84, 19.77.

The data indicate that the compound was synthesized correctly.

4) The compound 11 (0.8 mmol) was added into a flask, dissolved in 10 mL of dichloromethane, and added 6 vol % dichloromethane solution of dichloroacetic acid in 10 mL of ice-water bath. Stirring for 5 min, adding small amount of methanol to quench reaction, fading red, neutralizing with saturated sodium bicarbonate solution, extracting, drying with anhydrous sodium sulfate, concentrating, and separating by column chromatography to obtain the compound 13 (540 mg).

The nuclear magnetic resonance data are:

1H NMR (400 MHz, CDCl$_3$) δ 8.74 (s, 1H), 8.62 (d, J=73.6 Hz, 1H), 8.45 (dd, J=4.7, 3.5 Hz, 1H), 8.25 (d, J=3.3 Hz, 1H), 8.04-7.96 (m, 3H), 7.64 (dt, J=4.6, 1.5 Hz, 2H), 7.53 (ddd, J=29.9, 14.9, 7.4 Hz, 4H), 7.10 (ddd, J=5.2, 4.1, 2.4 Hz, 1H), 6.44 (dd, J=9.1, 5.5 Hz, 1H), 5.34 (t, J=5.5 Hz, 1H), 4.52-4.36 (m, 3H), 4.31 (dt, J=12.3, 6.0 Hz, 2H), 3.90 (dd, J=38.9, 12.8 Hz, 2H), 3.10 (t, J=6.3 Hz, 2H), 2.80 (t, J=6.0 Hz, 2H), 2.69 (dd, J=14.1, 5.4 Hz, 1H).

13C NMR (101 MHz, CDCl$_3$) δ 166.62, 164.98, 158.92, 152.14, 152.10, 150.81, 150.07, 149.86, 145.25, 144.40, 142.96, 137.29, 133.60, 133.26, 133.10, 132.14, 129.17, 128.95, 127.95, 127.84, 124.24, 121.29, 120.32, 116.49, 116.45, 87.63, 87.58, 87.05, 80.51, 77.28, 66.03, 62.85, 62.54, 62.50, 39.15, 39.11, 38.34, 38.27, 19.87, 19.80.

The data indicate that the compound was synthesized correctly.

5) The compound 11 (0.45 mmol) was added into a flask, 6 mL of acetonitrile and 2 mL of tert-butylamine were added to the flask, and after stirring at room temperature for 30 min, the solvent was removed by rotary evaporation to obtain the compound 12. The compound 13 (0.37 mmol) and 1-(mesitylene-2-sulfone)-3-nitro-1, 2, 4-triazole (1.11 mmol) were added thereto, and 15 mL of super dry pyridine was added thereto, followed by stirring at room temperature for 2 h. Adding a small amount of water to quench the reaction, removing the solvent by rotary evaporation, adding 20 mL of dichloromethane to dissolve, adding a proper amount of 5 wt % aqueous solution of oxalic acid, separating out the organic phase, drying, filtering, concentrating, adding 3 vol % dichloromethane solution of dichloroacetic acid, stirring for 5 min, adding a proper amount of methanol and saturated aqueous solution of sodium bicarbonate to neutralize, extracting, drying the organic phase, filtering, concentrating, and separating by column chromatography to obtain the compound 14 (350 mg).

The nuclear magnetic resonance data are:

1H NMR (400 MHz, CDCl3) δ 8.67 (dd, J=29.4, 8.5 Hz, 2H), 8.51-8.20 (m, 4H), 7.96 (t, J=8.9 Hz, 4H), 7.70-7.33 (m, 10H), 7.05 (dt, J=11.0, 7.2 Hz, 2H), 6.51 (dd, J=13.0, 6.4 Hz, 1H), 6.45-6.33 (m, 1H), 5.38 (s, 1H), 5.24 (dd, J=17.5, 5.5 Hz, 1H), 4.52-4.20 (m, 10H), 3.79 (dt, J=19.8, 11.3 Hz, 3H), 3.23-2.89 (m, 6H), 2.78 (d, J=18.5 Hz, 3H), 2.68-2.51 (m, 1H), 1.22 (s, 3H).

13C NMR (101 MHz, CDCl3) δ 165.07, 158.84, 158.77, 158.70, 152.58, 151.94, 151.49, 150.64, 150.18, 149.83, 149.76, 143.02, 141.81, 137.32, 133.41, 133.36, 132.85, 132.77, 128.77, 128.75, 128.69, 128.08, 128.05, 124.14, 123.59, 121.28, 121.21, 120.21, 120.12, 116.73, 87.40, 86.64, 84.54, 80.22, 77.33, 66.06, 65.77, 62.67, 38.92, 38.15, 38.08, 29.69, 19.86, 19.79, 0.02.

The data indicate that the compound was synthesized correctly.

6) The compound 14 (0.23 mmol) was added to tert-butylamine/acetonitrile (1:3, v/v) of the reaction solution, stirring at normal temperature for 20 min, removing the solvent by rotary evaporation, adding 100 mL of pyridine for dissolution, adding 1-(mesitylene-2-sulfone)-3-nitro-1, 2, 4-triazole (1.38 mmol), reacting at normal temperature for 4 h, removing the solvent, adding 20 mL of dichloromethane for dissolution, adding a proper amount of 5 wt % oxalic acid aqueous solution, separating out the organic phase, drying, filtering, concentrating, and separating by column chromatography to obtain the compound 15 (181 mg).

The nuclear magnetic resonance data are:

1H NMR (400 MHz, CDCl3) δ 9.76 (s, 2H), 8.76 (d, J=9.7 Hz, 2H), 8.53-8.36 (m, 2H), 8.36-8.18 (m, 2H), 7.68-7.55 (m, 3H), 7.37-7.26 (m, 5H), 7.14-6.98 (m, 8H), 6.45 (dd, J=13.8, 6.2 Hz, 2H), 5.71-5.36 (m, 2H), 4.93 (s, 4H), 4.66-4.32 (m, 9H), 4.12 (d, J=5.1 Hz, 1H), 3.67-3.34 (m, 2H), 3.11 (t, J=6.2 Hz, 4H), 2.73 (dd, J=13.3, 7.5 Hz, 2H), 1.26 (s, 2H).

13C NMR (101 MHz, CDCl3) δ 167.30, 158.86, 158.68, 158.57, 157.10, 157.06, 152.49, 152.42, 152.35, 151.38, 151.33, 151.24, 151.16, 149.81, 148.67, 148.60, 143.12, 142.92, 142.76, 142.55, 137.22, 137.18, 129.77, 123.49, 123.39, 123.28, 122.28, 122.26, 121.19, 120.10, 120.08, 114.85, 114.55, 85.58, 85.23, 83.03, 82.59, 79.03, 78.17, 77.84, 77.48, 77.36, 77.16, 76.84, 68.21, 66.14, 66.09, 65.93, 65.88, 65.44, 64.99, 53.52, 38.29, 38.23, 38.12, 38.05, 38.00, 36.29, 31.88, 29.65, 29.62, 29.32, 22.66, 14.13.

The data indicate that the compound was synthesized correctly.

7) The compound 15 (100 mg) was added into a flask, and 5 mL of methanol was added to dissolve it, 500 µL of diisopropylamine was added thereto, and the mixture was stirred at room temperature for 4 h, followed by spin-drying of the solvent and direct column chromatography to separate the compound 16 (65 mg).

The nuclear magnetic resonance data are:

1H NMR (400 MHz, CDCl3) δ 8.33 (d, J=8.4 Hz, 2H), 7.94 (d, J=8.1 Hz, 2H), 6.41 (dd, J=13.9, 7.4 Hz, 2H), 6.20 (d, J=30.1 Hz, 4H), 5.45 (d, J=59.0 Hz, 2H), 4.51 (dd, J=16.6, 8.1 Hz, 3H), 4.39 (t, J=8.3 Hz, 2H), 4.16 (tt, J=9.5, 4.9 Hz, 5H), 3.17 (dd, J=11.4, 6.6 Hz, 4H), 2.82-2.66 (m, 2H), 2.26 (s, 6H), 1.22 (d, J=13.3 Hz, 18H).

MALDI-TOF-HRMS: the relative molecular mass of C34H38N12O10P2S4 was 964.1192, and a peak of [M+H]+ 965.1271 was found.

The data indicate that the compound was synthesized correctly.

Comparative Example 1 cddA35 (structure shown in table 2) was prepared according to the method in the literature (Wang, B.; Wang, Z.; Javornik, U.; Xi, Z.; Plavec, J., Computational and NMR spectroscopy insights into the conformation of cyclic dinucleotides. Sci Rep 2017, 7 (1), 16550.).

cddA35 Nuclear Magnetic Resonance Data:

1H NMR (400 MHz, D20) δ 8.15 (s, 2H), 7.80 (s, 2H), 6.16 (d, J=6.4 Hz, 2H), 5.22-5.04 (m, 2H), 4.26 (d, J=9.8 Hz, 4H), 4.02 (dd, J=11.2, 4.1 Hz, 2H), 3.05-2.98 (m, 2H), 2.75-2.62 (m, 2H).

13C NMR (101 MHz, D20) δ 154.39, 151.78, 146.71, 139.32, 118.08, 84.87, 83.30, 83.19, 70.16, 62.25, 46.71, 39.01, 8.26.

The data indicate that the compound was synthesized correctly.

Test Example 1

Determination of the Oil-Water Partition Coefficient Log P of the Two Cyclic Dinucleotide Prodrug Molecules.

1) Preparing the compound solution: a certain amount of the compound 8, the compound 16 and the compound cddA35 were weighed and dissolved in DMSO solutions respectively to prepare mother solutions with a concentration of 1 mg/mL. 2) 20 µL of the prepared mother liquor was added to an EP tube containing a mixture of 1 mL of n-octanol and 1 mL of purified water (10 mM K2HPO4 pH7.0), vortexed for 2 h with shaking, and allowed to stand overnight at 4° C. for phase separation, and 400 µL of solution from each phase was separated. Centrifuging at 3000 rpm for 5 min, filtering with corresponding 0.22 µM filter membrane, measuring the two-phase absorption peak area under the same HPLC parameter condition, repeating the experiment for three times, and calculating log value of the peak area ratio of n-octyl alcohol phase and water phase to obtain the log P value of the target compound, as shown in Table 2.

HPLC conditions: the instrument used by an Agilent 1260 HPLC, column: Agilent ZORABX SB-C185 µm [4.6×150 mm], column temperature 25° C., sample injection 10 µL, detection wavelength was 254 nM, chromatographic gradient method as shown in Table 1 below.

TABLE 1

| HPLC liquid phase gradient method | | | |
|---|---|---|---|
| Time (min) | Vol % A(10 mM TEAA buffer solution) | Vol % B (MeCN) | Flow rate (mL/min) |
| 1 | 98 | 2 | 1 |
| 6 | 0 | 100 | 1 |
| 10 | 0 | 100 | 1 |
| 13 | 98 | 2 | 1 |
| 15 | 98 | 2 | 1 |

TABLE 2

| Compound | Structure | logP |
|---|---|---|
| Compound8 | 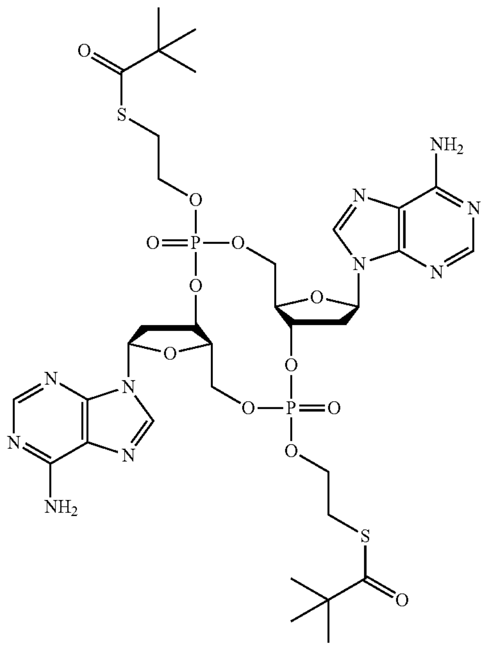 | 1.93 ± 0.01 |
| Compound16 | 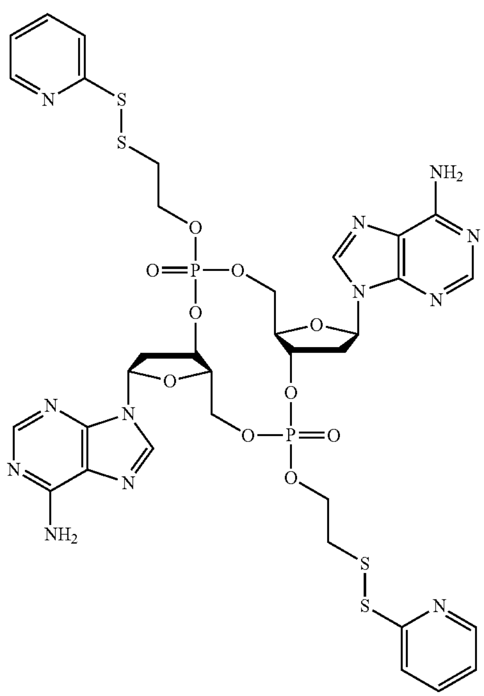 | 0.85 ± 0.02 |

TABLE 2-continued

| Compound | Structure | logP |
|---|---|---|
| cddA35 | 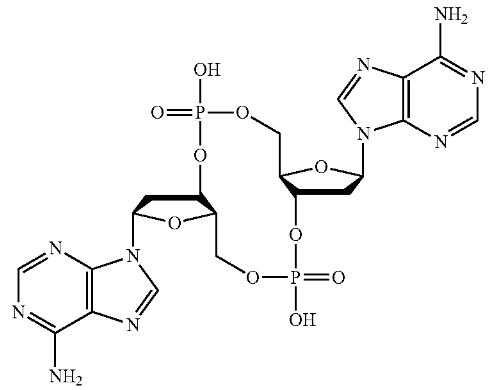 | −3.43 ± 0.06 |

As can be seen from the results in Table 2, the log P of the phosphate ester protected with the substituted mercaptoethanol is greatly improved. Compared with cddA35 without the exposed negative phosphate charge, the log P value of the cddA35 is −3.43, and the cddA35 is basically free of lipid solubility. And the log P of the compound 8 protected by thioacyl ethyl ester and the compound 16 protected by dimercapto ethanol is 1.93 and 0.85, respectively, so that the lipophilicity is greatly improved, and the compound is favorable for penetrating a cell membrane and entering cells to play an immune stimulator role.

Test Example 2

Activity assay of two cyclic dinucleotide prodrug molecules in HEK293T cells

The principle is as follows: dual-fluorescence reporter gene experiments: After entering a cell, the cyclic dinucleotide prodrug molecule passes through thioesterase in the cytoplasm of the cell or a reducing environment, so that thioester bond breakage or disulfide bond breakage is carried out, then an intermediate is obtained, a sulfur atom at a p position can nucleophilically attack a carbon atom at the a position, cyclic thioethane is removed, cyclic dinucleotides with a phosphodiester structure of a parent drug with negative charges are released, the intracellular STING protein is combined and activated, interferon regulatory factor 3 (IRF3) is phosphorylated, phosphorylated IRF3 enters into the nucleus and combined with the promoter region of a interferon-β gene to cause the expression of interferon, and based on these, the interferon gene promoter is introduced into a promoter of firefly luciferase, so that the cell activity of the prodrug molecule can be measured by using a dual-fluorescence reporter gene method.

Experimental Materials:

(1) preparing the compound solution: the compound 8 and the compound 16 were dissolved in DMSO, respectively, to obtain a final concentration of 1 mM. cddA35 was dissolved in water and similarly prepared at a concentration of 1 mM.

(2) Plasmid solution preparation: the pcDNA3.1-hSTING-wt plasmid was formulated to have a concentration of 400 ng/μL, the pGL3-IFNβ plasmid was formulated to have a concentration of 400 ng/μL, and the pGL4.74-Rluc plasmid was formulated to have a concentration of 100 ng/μL.

The test method includes the following steps:

HEK293T cells confluence reached about 70%, and the original culture medium is changed to 500 mL of a serum-free culture medium opti-DMEM to be transferred. The above component solutions were prepared, which included pcDNA3.1-hsting-wt 2 μL, pGL3-IFNβ 1 μL, pGL4.74-Rluc 1 μL, opti-DMEM medium supplemented 50 μL/well, four wells in parallel. The above solution mixture was mixed by adding 50 μL of 2/50 Lipo2000 transfection solution, the mixture was left to stand at room temperature for 15 min and then mixed well, and 100 μL/well of transfection was added and after 4 h 1 mL of DMEM medium at 37° C./well was added. After 18 h, the medium was further changed to 500 mL opti-DMEM with or without serum. 8 μL (5 μM) of the compound 8, the compound 16 or cddA35 and 92 μL of opti-DMEM mixed and left for 15 min, transfected at 100 μL/well. After 4 h, 1 mL of DMEM medium at 37° C./well was added. After 24 h, the dual-fluorescence results were detected, as shown in FIG. 1.

Figure 1:
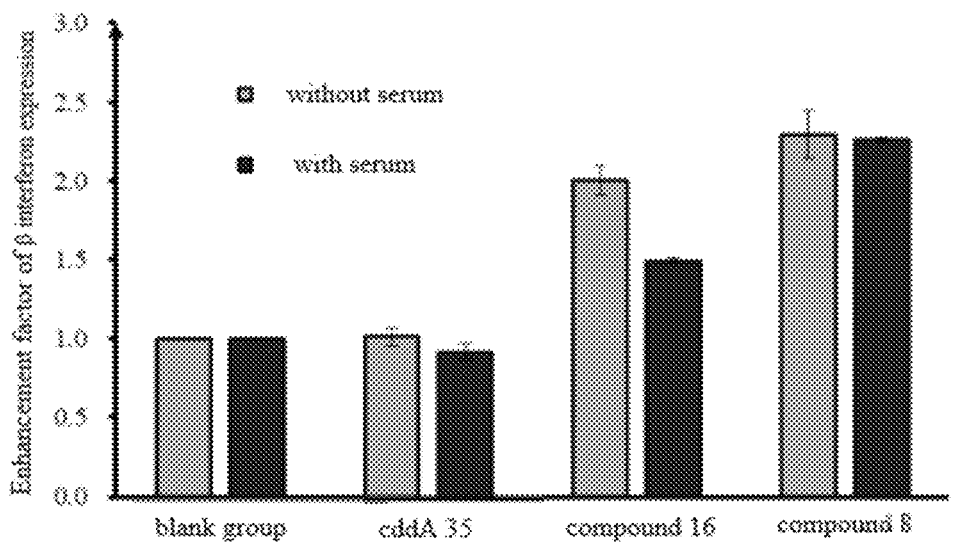
FIG. 1 is the results of the dual fluorescence test in Test Example 2.

From the results shown in FIG. 1, it can be seen that the unmodified highly electronegative cyclic dinucleotide cddA hardly crosses cell membranes, and the two cyclic dinucleotide compound 8 and compound 16 protected by phosphotriester provided by the present invention can autonomously cross cell membranes without any transfection reagent, and release the parent drug molecule cddA35 in cytoplasm due to thioesterase or reducing environment, so as to activate STING pathway and cause the expression of interferon.

Test Example 3

Figure 2:
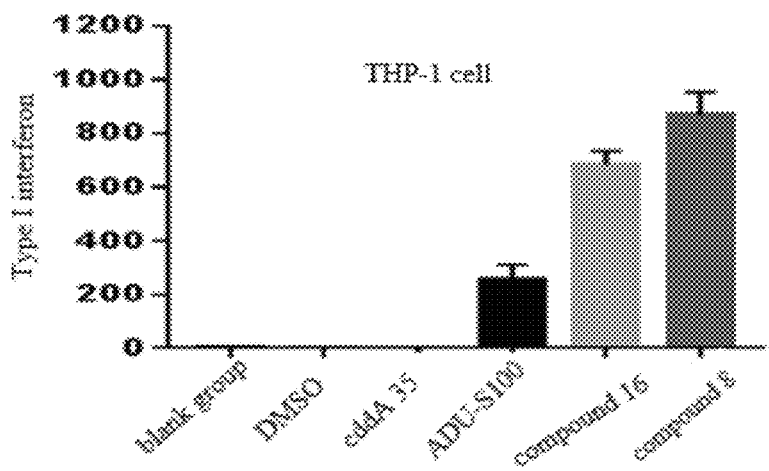
FIG. 2 is the results of the type I interferon test in the monocyte line THP-1 in Test Example 3.
Figure 3:
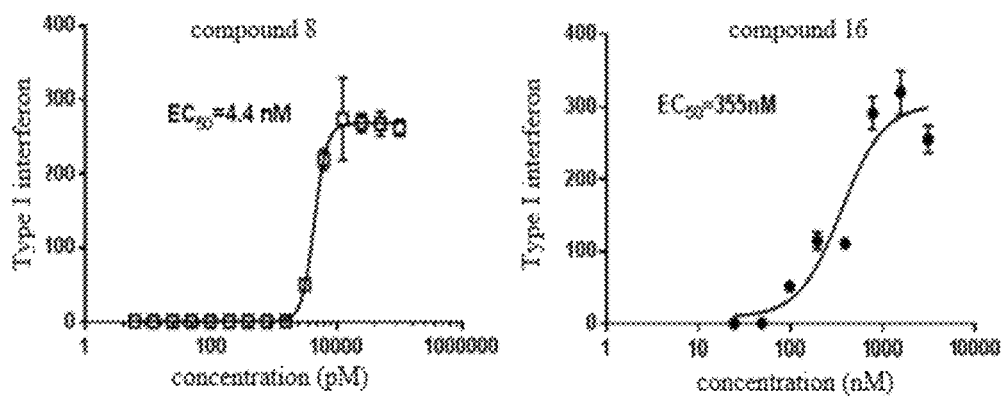
FIG. 3 is the $EC_{50}$ value of the compound in Test Example 3 causing type I interferon expression in THP-1 cells.

Activity Assay of Two Cyclic Dinucleotide Prodrug Molecules in Monocytic Cell Line THP-1 Cells The test method includes the following steps:

The THP-1-Lucia cells confluency reached about 80%, and the compound 8, the compound 16 and the drug ADU-S100 are directly dissolved into a culture medium according to a certain concentration and added into a 24-well plate, wherein four wells are parallel. The cells were maintained under the culture condition of 37° C. and 5% CO2 for 24 h. After the end of the culture, luciferase activity was measured. Wherein, the test results of the type I interferon of the compound 8, the compound 16 and the drug ADU-S100 in the monocyte cell line THP-1 under the action concentration of 10 μM are shown in FIG. 2; EC50 values for the compound 8 and the compound 16 to cause type I interferon expression in THP-1 cell lines were then determined by dose-response curves for serial dilutions at various concentrations, as shown in FIG. 3.

From the results shown in FIG. 2, it can be seen that both the compound 8 and the compound 16 cause strong expression of type I interferon in the monocyte THP-1 cell line at the action concentration of 10 μM without any transfection reagent, and the activity is much higher than that of the drug ADU-S100, which has entered clinical phase II. As can be seen from FIG. 3, the EC50 values of the compound 8 and the compound 16, which cause type I interferon expression in THP-1 cell line, were 4.4 nM and 355 nM, respectively. Compared to the EC50 value of the control drug ADU-S100 (reference compound 2'3'-RR-(AXA) in patent CN108430503A, the EC50 value was 41.5 μM), the EC50 values of the compound 16 and the compound 8 were 9430-fold and 117-fold increased, respectively, and the activity was considerably increased.

Test Example 4

Anticancer Activity Assay of the Compound 8
Experimental Materials:

Mice: BABL/C female mice, weight 18 g to 22 g. The source is the animal experiment center in Guangdong province, and the mice are fed with pellet feed and freely eat and drink water.
Tumor Cell Lines: CT-26-Luc Cells Establishing a mouse tumor model: the cells are cultured and passaged, the cells are collected in the logarithmic phase of the cells and prepared into cell suspension with the concentration of (1.0×107) per milliliter, 0.1 mL of cell suspension (the number of the cells is 1.0×106 per mouse) is injected into the armpit of the right forelimb, the tumor grows to be about 5 mm in diameter successfully, and the mice are divided into three groups randomly after about 10 days.
Negative Control Group: Physiological Saline Solution Positive control group: ADU-S100 (clinical phase II drug) at a dose of 1 mg/kg
Experimental Groups: The Compound 8 at a Dose of 1 mg/kg The administration method includes the following steps: the administration was started at the 10th day after tumor inoculation growth, and 50 microliters/mouse was administered once every two days for a total of three times by intratumoral injection. The growth of tumors in mice was detected by chemiluminescence using the IVIS Spectrum Imaging System. Before imaging, small molecule fluorescein preparation: an appropriate amount of 15 mg/mL sodium fluorescein salt was prepared in PBS solution, and sodium fluorescein was ordered from Shanghai Yeasen Biotech Co., Ltd. Oxygen and isoflurane are prepared in advance. Mice were placed in an anesthesia box by intraperitoneal injection of 100 μL of fluorescein, and after the animals were anesthetized, the mice were transferred to an imaging chamber in an imager. The posture of the mice was adjusted as needed. The imaging parameters are as follows: automatic exposure, wherein the Binning value is 2, and the F value is 8. The imaging time was chosen to be 10 min. After imaging, fluorescence values were converted to photon numbers and the total number of fluorescence photons for each experimental group was counted. The imager is an IVIS Spectrum imaging platform of Perkinelmer company. The results are shown in FIG. 4. In which the numbers in FIG. 4a, FIG. 4b, FIG. 4c, FIG. 4d, FIG. 4e and FIG. 4f represent the total number of fluorescence photons in the circular region (ROI, region of interest), and FIG. 4g and FIG. 4h are statistical graphs of the total number of fluorescence photons for each experimental group, respectively.

The tumor volume size and survival rate results for each group of mice are shown in FIG. 5. Wherein, the tumor volume is measured by a vernier caliper to obtain the length and width of the tumor, and the tumor volume is calculated according to a formula (volume=length×width×width/2), and the survival rate=the value of mice with the tumor volume less than 2000 cubic millimeters in each experimental group/the total value of mice in each experimental group.

From the results shown in FIG. 4 and FIG. 5, it can be seen that in the CT-26 mouse tumor model, the growth of the tumor in the mice were only controlled compared to the control drug ADU-S100 at the dose of 1 mg/kg, and the tumor in the experimental group by using the compound 8 of the present invention was substantially disappeared, thereby indicating that the compound 8 has a better anti-tumor activity and an effect superior to that of the clinical drug ADU-S100.

The invention claimed is:
1. A cyclic dinucleotide prodrug molecule, wherein the cyclic dinucleotide prodrug molecule has any one of structures represented by formula (1) to formula (10):

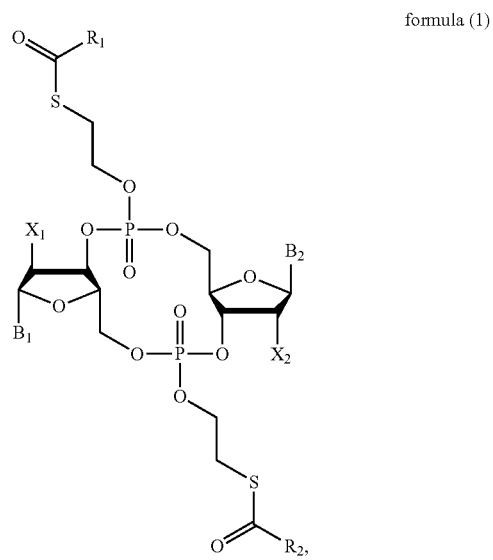

formula (1)

formula (2)
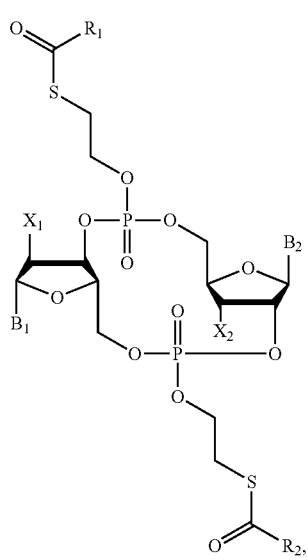
formula (3)
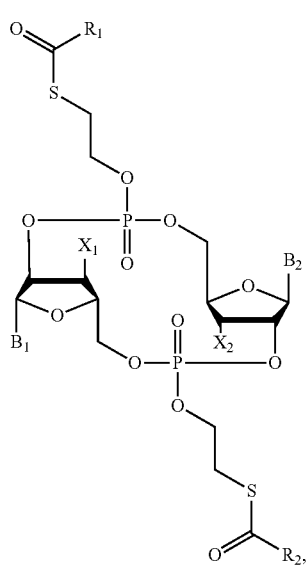
formula (4)
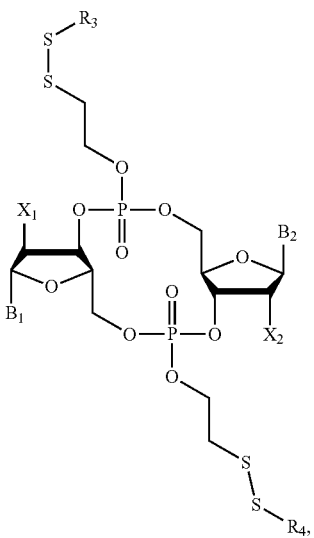
formula (5)
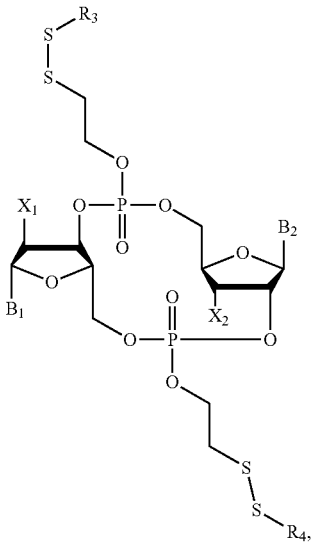
formula (6)
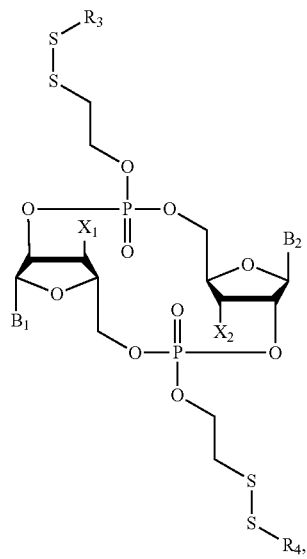
formula (7)
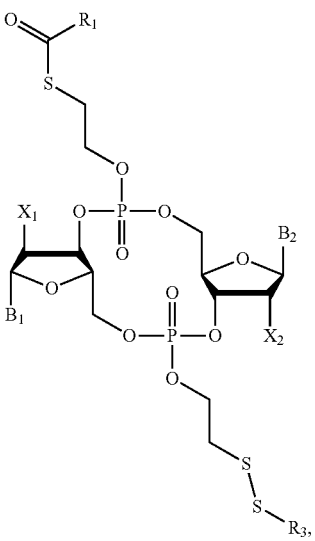

-continued formula (8)

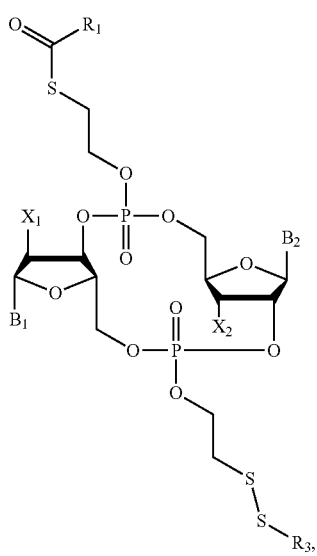

formula (9)

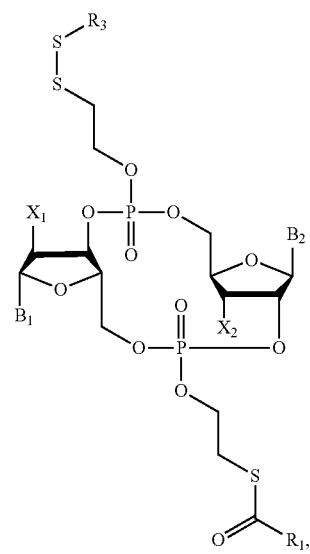

formula (10)

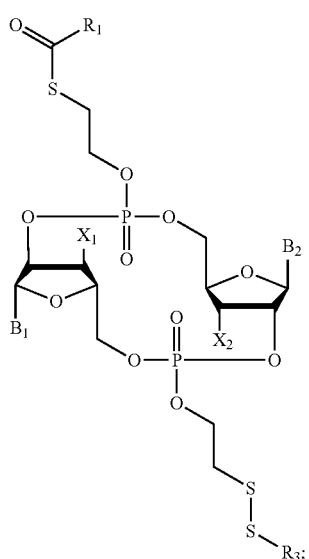

wherein, in formula (1) to formula (10), both $B_1$ and $B_2$ are adenine;

both $X_1$ and $X_2$ are —H;

$R_1$, $R_2$, $R_3$ and $R_4$ are the same and are selected from the group consisting of substituted or unsubstituted aliphatic hydrocarbon groups of $C_1$-$C_6$, substituted or unsubstituted aromatic hydrocarbon groups of $C_6$-$C_{11}$ and five-membered or six-membered heterocyclic groups; and the substituents optionally present in $R_1$, $R_2$, $R_3$ and $R_4$ are selected from the group consisting of $C_1$-$C_5$ alkyl groups.

2. The cyclic dinucleotide prodrug molecule as claimed in claim 1, wherein the cyclic dinucleotide prodrug molecule has a structure represented by formula (11), formula (11)

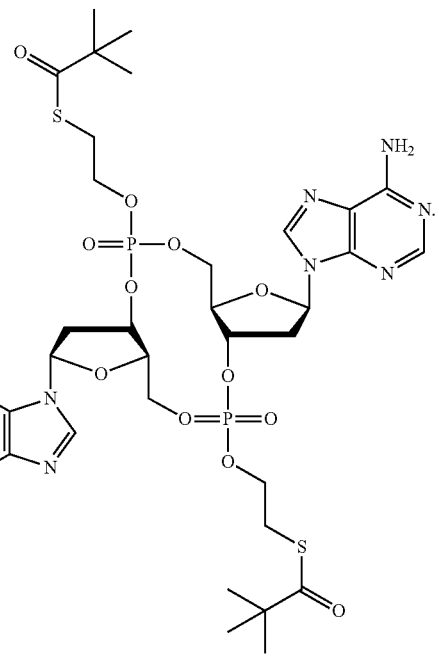

3. The cyclic dinucleotide prodrug molecule as claimed in claim 1, wherein the cyclic dinucleotide prodrug molecule has a structure represented by formula (12), formula (12)

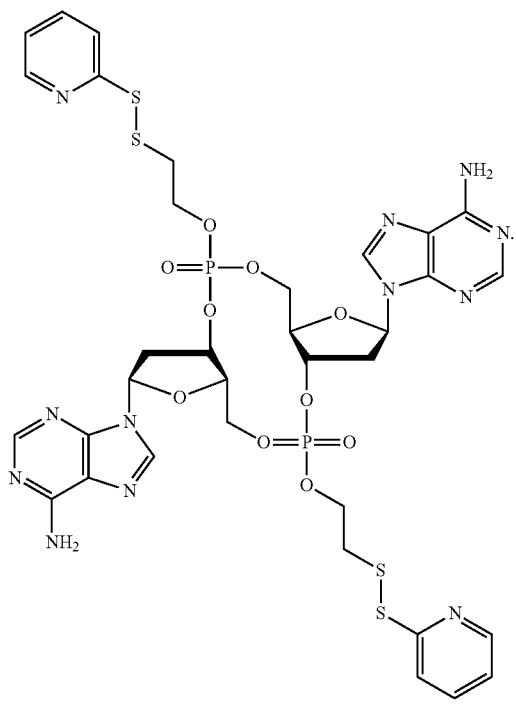

4. A method of preparing the cyclic dinucleotide prodrug molecule as claimed in claim 1, comprising:
   a) carrying out a first contact reaction on a first nucleotide monomer compound, a second nucleotide monomer compound and a first condensing agent in a first liquid reaction medium to obtain a linear dinucleotide intermediate;
   b) under an alkaline condition, the linear dinucleotide intermediate is subjected to decyanoethyl reaction, and then the obtained reaction product and a second condensing agent are subjected to second contact reaction in a second liquid reaction medium to obtain a cyclic dinucleotide prodrug molecule with a protecting group;
   c) carrying out deprotection reaction on the cyclic dinucleotide prodrug molecule with the protecting group obtained after the second contact reaction is carried out to obtain the cyclic dinucleotide prodrug molecule;
   wherein the first nucleotide monomer compound has a structure represented by formula (13) or formula (14):

formula (13)

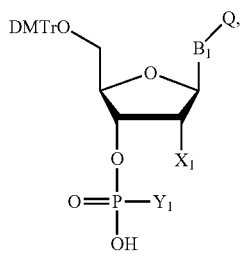

formula (14)

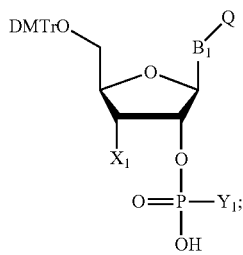

the second nucleotide monomer compound has a structure represented by formula (15) or formula (16):

formula (15)

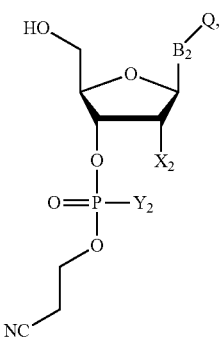

formula (16)

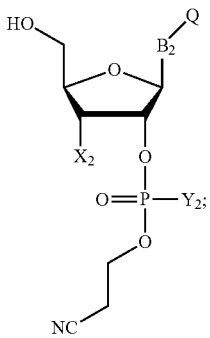

wherein Q represents the protecting group on an exocyclic amino group in the bases represented by $B_1$ and $B_2$, and the protecting group is a phenoxyacetyl group or a 4-isopropylphenoxyacetyl group;

both the first condensing agent and the second condensing agent are 1-(mesitylene-2-sulfone)-3-nitro-1, 2, 4-triazole;

the alkaline conditions are provided by a solution of tert-butylamine in acetonitrile.

5. The method as claimed in claim 4, wherein the first contact reaction is carried out at a temperature in a range of 0° C. to 50° C. for a time of from 2 h to 8 h.

6. The method as claimed in claim 4, wherein the deprotection reaction is carried out in the presence of a mixed solution of diisopropylamine and methanol in a volume ratio of 1:5 to 1:20.

7. The method as claimed in claim 4, wherein the conditions for carrying out the second contact reaction is carried out at a temperature of from 0° C. to 50° C. for a time of from 2 h to 8 h.

8. The method as claimed in claim 4, in step a), the first condensing agent is used in an amount of 2 mol to 3 mol with respect to 1 mol of the first nucleotide monomer compound.

9. The method as claimed in claim 4, in step b), the second condensing agent is used in an amount of 4 mol to 5 mol with respect to 1 mol of the linear dinucleotide intermediate.

10. The method as claimed in claim 4, wherein in step b), the alkaline conditions are provided by a mixed solution of tert-butylamine and acetonitrile in a volume ratio of 1:1 to 1:5.

11. A stereoisomer, a tautomer, a nitrogen oxide, a solvate, or a pharmaceutically acceptable salt of the cyclic dinucleotide prodrug molecule of claim 1.

* * * * *